(12) United States Patent
McGurk et al.

(10) Patent No.: US 7,766,938 B2
(45) Date of Patent: Aug. 3, 2010

(54) PLEURAL EFFUSION TREATMENT DEVICE, METHOD AND MATERIAL

(75) Inventors: Erin McGurk, Palo Alto, CA (US);
Ronald Dieck, Palo Alto, CA (US);
Charles Wartchow, Belmont, CA (US);
Glen Gong, San Francisco, CA (US);
Jobert Balceta, San Jose, CA (US)

(73) Assignee: PneumRx, Inc., Mountain View, CA (US)

( * ) Notice: Subject to any disclaimer, the term of this patent is extended or adjusted under 35 U.S.C. 154(b) by 1394 days.

(21) Appl. No.: 11/177,926

(22) Filed: Jul. 8, 2005

(65) Prior Publication Data

US 2006/0009801 A1    Jan. 12, 2006

Related U.S. Application Data

(60) Provisional application No. 60/586,887, filed on Jul. 8, 2004.

(51) Int. Cl.
*A61B 17/08* (2006.01)
(52) U.S. Cl. ...................... 606/214; 530/350
(58) Field of Classification Search ................ 606/214; 530/350
See application file for complete search history.

(56) References Cited

U.S. PATENT DOCUMENTS

| | | |
|---|---|---|
| 3,527,841 A | 9/1970 | Wicker, Jr. et al. |
| 3,559,652 A | 2/1971 | Banitt et al. |
| 3,722,599 A | 3/1973 | Robertson et al. |
| 3,940,362 A | 2/1976 | Overhults |
| 3,995,641 A | 12/1976 | Kronenthal et al. |
| 4,013,080 A | 3/1977 | Froning |
| 4,153,058 A | 5/1979 | Nehme |
| 4,233,984 A | 11/1980 | Walling |
| 4,418,052 A | 11/1983 | Wong |
| 4,479,792 A | 10/1984 | Lazarus et al. |
| 4,532,935 A | 8/1985 | Wang |
| 4,656,254 A | 4/1987 | Shearer et al. |
| 4,702,260 A | 10/1987 | Wang |
| 4,739,760 A | 4/1988 | Chin et al. |
| 4,766,906 A | 8/1988 | Wang |
| 4,769,017 A | 9/1988 | Fath et al. |
| 4,880,015 A | 11/1989 | Nierman |
| 5,008,245 A | 4/1991 | Digenis et al. |
| 5,011,686 A | 4/1991 | Pang |
| 5,024,829 A | 6/1991 | Berger et al. |
| 5,056,529 A | 10/1991 | de Groot |
| 5,084,012 A | 1/1992 | Kelman |
| 5,108,368 A | 4/1992 | Hammerslag et al. |
| 5,162,307 A | 11/1992 | Digenis et al. |
| 5,165,420 A | 11/1992 | Strickland |
| 5,186,167 A | 2/1993 | Kolobow |
| 5,190,546 A | 3/1993 | Jervis |
| 5,219,895 A | 6/1993 | Kelman |
| 5,240,011 A | 8/1993 | Assa |
| 5,261,889 A | 11/1993 | Laine et al. |
| 5,283,173 A | 2/1994 | Fields et al. |
| 5,292,362 A * | 3/1994 | Bass et al. ............ 106/173.01 |
| 5,312,329 A | 5/1994 | Beaty et al. |
| 5,312,331 A | 5/1994 | Knoepfler |
| 5,315,992 A | 5/1994 | Dalton |
| 5,328,687 A | 7/1994 | Leung et al. |
| 5,334,183 A | 8/1994 | Wuchinich |
| 5,354,287 A | 10/1994 | Wacks |
| 5,385,606 A | 1/1995 | Kowanko |
| 5,423,830 A | 6/1995 | Schneebaum et al. |
| 5,478,925 A | 12/1995 | Wallach et al. |
| 5,484,401 A | 1/1996 | Rodriguez et al. |
| 5,514,371 A | 5/1996 | Leung et al. |
| 5,514,372 A | 5/1996 | Leung et al. |
| 5,514,536 A | 5/1996 | Taylor |
| 5,526,821 A | 6/1996 | Jamshidi |
| 5,549,904 A | 8/1996 | Juergensen et al. |
| 5,575,997 A | 11/1996 | Leung et al. |
| 5,582,834 A | 12/1996 | Leung et al. |
| 5,583,114 A | 12/1996 | Barrows et al. |
| 5,599,294 A | 2/1997 | Edwards et al. |
| 5,660,175 A | 8/1997 | Dayal |

(Continued)

FOREIGN PATENT DOCUMENTS

EP    0367514 A2    5/1990

(Continued)

OTHER PUBLICATIONS

Karlinsky et al. ,Chest 89, 146-148 (1986).*

(Continued)

*Primary Examiner*—Chih-Min Kam
(74) *Attorney, Agent, or Firm*—Townsend and Townsend and Crew LLP

(57) ABSTRACT

The invention discloses a method of treating a patient for pleural effusion comprising percutaneously delivering an adhesive material to a pleural space of the patient. Suitable adhesive materials for performing any of the embodiments of the methods of the invention can be selected from the group consisting of hydrogels, collagen, poly(lactic acid), poly(g-lycolide), cyanoacrylates, glutaraldehyde, PEG, protein, and polysaccharide and derivatives thereof. The invention also discloses a pleural effusion treatment apparatus comprising an adhesive material adapted to adhere pleural membranes defining a pleural space and a pleural space access member adapted to deliver the adhesive material to the pleural space.

14 Claims, 9 Drawing Sheets

U.S. PATENT DOCUMENTS

| | | |
|---|---|---|
| 5,660,185 A | 8/1997 | Shmulewitz et al. |
| 5,663,299 A | 9/1997 | Remold-O'Donnell |
| 5,667,973 A | 9/1997 | Fields et al. |
| 5,697,365 A | 12/1997 | Pell |
| 5,735,264 A | 4/1998 | Siczek et al. |
| 5,736,132 A | 4/1998 | Juergensen et al. |
| 5,739,288 A | 4/1998 | Edwardson et al. |
| 5,750,657 A | 5/1998 | Edwardson et al. |
| 5,827,672 A | 10/1998 | Remold-O'Donnell |
| 5,846,235 A | 12/1998 | Pasricha et al. |
| 5,916,210 A | 6/1999 | Winston |
| 5,916,212 A | 6/1999 | Baust et al. |
| 5,928,611 A | 7/1999 | Leung |
| 5,938,635 A | 8/1999 | Kuhle |
| 5,954,636 A | 9/1999 | Schwartz et al. |
| 5,957,919 A | 9/1999 | Laufer |
| 5,964,770 A | 10/1999 | Flomenblit et al. |
| 5,972,026 A | 10/1999 | Laufer et al. |
| 5,978,697 A | 11/1999 | Maytal et al. |
| 5,981,621 A | 11/1999 | Clark et al. |
| 6,010,714 A | 1/2000 | Leung et al. |
| 6,066,090 A | 5/2000 | Yoon |
| 6,080,113 A | 6/2000 | Heneveld et al. |
| 6,083,255 A | 7/2000 | Laufer et al. |
| 6,087,325 A | 7/2000 | Meers et al. |
| 6,174,323 B1 | 1/2001 | Biggs et al. |
| 6,183,498 B1 | 2/2001 | DeVore et al. |
| 6,200,333 B1 | 3/2001 | Laufer |
| 6,258,100 B1 | 7/2001 | Alferness et al. |
| 6,267,732 B1 | 7/2001 | Heneveld et al. |
| 6,273,907 B1 | 8/2001 | Laufer |
| 6,283,988 B1 | 9/2001 | Laufer et al. |
| 6,283,989 B1 | 9/2001 | Laufer et al. |
| 6,287,290 B1 | 9/2001 | Perkins et al. |
| 6,287,304 B1 | 9/2001 | Eggers et al. |
| 6,293,951 B1 | 9/2001 | Alferness et al. |
| 6,299,633 B1 | 10/2001 | Laufer |
| 6,310,036 B1 | 10/2001 | Browdie |
| 6,310,166 B1 | 10/2001 | Hickey et al. |
| 6,312,428 B1 | 11/2001 | Eggers et al. |
| 6,315,737 B1 | 11/2001 | Skinner |
| 6,328,689 B1 | 12/2001 | Gonzalez et al. |
| 6,328,701 B1 | 12/2001 | Terwilliger |
| 6,329,337 B1 | 12/2001 | Morita et al. |
| 6,352,503 B1 | 3/2002 | Matsui et al. |
| 6,352,716 B1 | 3/2002 | Janoff et al. |
| 6,372,229 B1 | 4/2002 | Ollerenshaw et al. |
| 6,375,926 B1 | 4/2002 | Barnes et al. |
| 6,379,373 B1 | 4/2002 | Sawhney et al. |
| 6,387,044 B1 | 5/2002 | Tachibana et al. |
| 6,390,967 B1 | 5/2002 | Forman et al. |
| 6,398,775 B1 | 6/2002 | Perkins et al. |
| 6,402,701 B1 | 6/2002 | Kaplan et al. |
| 6,402,754 B1 | 6/2002 | Gonzalez |
| 6,411,852 B1 | 6/2002 | Danek et al. |
| 6,416,554 B1 | 7/2002 | Alferness et al. |
| 6,443,944 B1 | 9/2002 | Doshi et al. |
| 6,447,534 B2 | 9/2002 | Cragg et al. |
| 6,464,648 B1 | 10/2002 | Nakamura |
| 6,478,730 B1 | 11/2002 | Bala et al. |
| 6,485,407 B2 | 11/2002 | Alferness et al. |
| 6,485,436 B1 | 11/2002 | Truckai et al. |
| 6,488,673 B1 | 12/2002 | Laufer et al. |
| 6,491,706 B1 | 12/2002 | Alferness et al. |
| 6,494,844 B1 | 12/2002 | Van Bladel et al. |
| 6,494,896 B1 | 12/2002 | D'Alessio et al. |
| 6,494,897 B2 | 12/2002 | Sterman et al. |
| 6,500,461 B2 | 12/2002 | Perkins et al. |
| 6,509,031 B1 | 1/2003 | Miller et al. |
| 6,512,023 B1 | 1/2003 | Malofsky et al. |
| 6,514,290 B1 | 2/2003 | Loomas |
| 6,514,522 B2 | 2/2003 | Domb |
| 6,527,761 B1 | 3/2003 | Soltesz et al. |
| 6,537,195 B2 | 3/2003 | Forman |
| 6,537,314 B2 | 3/2003 | Langberg et al. |
| 6,540,694 B1 | 4/2003 | Van Bladel et al. |
| 6,540,716 B1 | 4/2003 | Holm |
| 6,549,800 B1 | 4/2003 | Atalar et al. |
| 6,551,255 B2 | 4/2003 | Van Bladel et al. |
| 6,551,302 B1 | 4/2003 | Rosinko et al. |
| 6,552,172 B2 | 4/2003 | Marx et al. |
| 6,558,337 B2 | 5/2003 | Dvorak et al. |
| 6,565,842 B1 | 5/2003 | Sojomihardjo et al. |
| 6,568,387 B2 | 5/2003 | Davenport et al. |
| 6,569,166 B2 | 5/2003 | Gonzalez |
| 6,577,893 B1 | 6/2003 | Besson et al. |
| 6,585,639 B1 | 7/2003 | Kotmel et al. |
| 6,589,161 B2 | 7/2003 | Corcoran |
| 6,592,559 B1 | 7/2003 | Pakter et al. |
| 6,592,594 B2 | 7/2003 | Rimbaugh et al. |
| 6,599,311 B1 | 7/2003 | Biggs et al. |
| 6,610,043 B1 | 8/2003 | Ingenito |
| 6,622,731 B2 | 9/2003 | Daniel et al. |
| 6,629,951 B2 | 10/2003 | Laufer et al. |
| 6,632,222 B1 | 10/2003 | Edwards et al. |
| 6,632,239 B2 | 10/2003 | Snyder et al. |
| 6,632,243 B1 | 10/2003 | Zadno-Azizi et al. |
| 6,634,363 B1 | 10/2003 | Danek et al. |
| 6,638,275 B1 | 10/2003 | McGaffigan et al. |
| 6,652,516 B1 | 11/2003 | Gough |
| 6,652,520 B2 | 11/2003 | Moorman et al. |
| 6,653,525 B2 | 11/2003 | Ingenito et al. |
| 6,663,624 B2 | 12/2003 | Edwards et al. |
| 6,679,264 B1 | 1/2004 | Deem et al. |
| 6,682,520 B2 | 1/2004 | Ingenito |
| 6,685,626 B2 | 2/2004 | Wironen |
| 6,689,072 B2 | 2/2004 | Kaplan et al. |
| 6,690,976 B2 | 2/2004 | Fenn et al. |
| 6,692,494 B1 | 2/2004 | Cooper et al. |
| 6,694,979 B2 | 2/2004 | Deem et al. |
| 6,695,791 B2 | 2/2004 | Gonzalez |
| 6,709,401 B2 | 3/2004 | Perkins et al. |
| 6,709,408 B2 | 3/2004 | Fisher |
| 6,709,456 B2 | 3/2004 | Langberg et al. |
| 6,712,812 B2 | 3/2004 | Roschak et al. |
| 6,716,180 B2 | 4/2004 | Fontenot |
| 6,723,095 B2 | 4/2004 | Hammerslag |
| 6,730,044 B2 | 5/2004 | Stephens et al. |
| 6,734,006 B2 | 5/2004 | Xiao et al. |
| 6,736,822 B2 | 5/2004 | McClellan et al. |
| 6,749,606 B2 | 6/2004 | Keast et al. |
| 6,752,767 B2 | 6/2004 | Turovskiy et al. |
| 6,752,812 B1 | 6/2004 | Truwit |
| 6,753,164 B2 | 6/2004 | Ni et al. |
| 6,758,824 B1 | 7/2004 | Miller et al. |
| 6,768,425 B2 | 7/2004 | Flaherty et al. |
| 6,770,066 B1 | 8/2004 | Weaver et al. |
| 6,770,070 B1 | 8/2004 | Balbierz |
| 6,774,216 B2 | 8/2004 | Ruben et al. |
| 6,784,153 B1 | 8/2004 | Rajotte et al. |
| 6,789,545 B2 | 9/2004 | Littrup et al. |
| 6,790,172 B2 | 9/2004 | Alferness et al. |
| 6,790,185 B1 | 9/2004 | Fisher et al. |
| 6,797,001 B2 | 9/2004 | Mathis et al. |
| 6,807,446 B2 | 10/2004 | Fenn et al. |
| 6,808,525 B2 | 10/2004 | Latterell et al. |
| 6,817,973 B2 | 11/2004 | Merril et al. |
| 6,825,091 B2 | 11/2004 | Bae et al. |
| 6,827,086 B2 | 12/2004 | Shuman |
| 6,830,756 B2 | 12/2004 | Hnojewyj |
| 6,840,243 B2 | 1/2005 | Deem et al. |
| 6,840,948 B2 | 1/2005 | Albrecht et al. |
| 6,840,952 B2 | 1/2005 | Saker et al. |
| 6,843,767 B2 | 1/2005 | Corcoran et al. |

| Patent Number | Date | Inventor |
|---|---|---|
| 6,849,262 B2 | 2/2005 | Ollerenshaw et al. |
| 6,852,108 B2 | 2/2005 | Barry et al. |
| 6,860,847 B2 | 3/2005 | Alferness et al. |
| 6,863,676 B2 | 3/2005 | Lee et al. |
| 6,875,209 B2 | 4/2005 | Zvuloni et al. |
| 6,878,106 B1 | 4/2005 | Herrmann |
| 6,878,141 B1 | 4/2005 | Perkins et al. |
| 6,886,558 B2 | 5/2005 | Tanaka |
| 6,901,927 B2 | 6/2005 | Deem et al. |
| 6,902,526 B2 | 6/2005 | Katzman |
| 6,902,536 B2 | 6/2005 | Manna et al. |
| 6,904,909 B2 | 6/2005 | Andreas et al. |
| 6,908,440 B2 | 6/2005 | Fisher |
| 6,918,881 B2 | 7/2005 | Miller et al. |
| 6,936,014 B2 | 8/2005 | Vetter et al. |
| 6,942,627 B2 | 9/2005 | Huitema |
| 6,945,942 B2 | 9/2005 | Van Bladel et al. |
| 6,962,587 B2 | 11/2005 | Johnson et al. |
| 6,964,662 B2 | 11/2005 | Kidooka |
| 6,967,673 B2 | 11/2005 | Ozawa et al. |
| 2001/0031948 A1 | 10/2001 | Cruise et al. |
| 2001/0047187 A1 | 11/2001 | Milo et al. |
| 2002/0007831 A1 | 1/2002 | Davenport et al. |
| 2002/0022588 A1 | 2/2002 | Wilkie et al. |
| 2002/0026188 A1 | 2/2002 | Balbierz et al. |
| 2002/0042564 A1 | 4/2002 | Cooper et al. |
| 2002/0042565 A1 | 4/2002 | Cooper et al. |
| 2002/0062120 A1 | 5/2002 | Perkins et al. |
| 2002/0071843 A1 | 6/2002 | Li et al. |
| 2002/0077593 A1 | 6/2002 | Perkins et al. |
| 2002/0086842 A1 | 7/2002 | Plank et al. |
| 2002/0086852 A1 | 7/2002 | Cantor et al. |
| 2002/0091379 A1 | 7/2002 | Danek et al. |
| 2002/0106411 A1 | 8/2002 | Wironen et al. |
| 2002/0111620 A1 | 8/2002 | Cooper et al. |
| 2002/0112729 A1 | 8/2002 | DeVore et al. |
| 2002/0128647 A1 | 9/2002 | Roschak et al. |
| 2002/0138074 A1 | 9/2002 | Keast et al. |
| 2002/0141966 A1* | 10/2002 | Dang ............... 424/78.37 |
| 2002/0147462 A1 | 10/2002 | Mair et al. |
| 2002/0161399 A1 | 10/2002 | Cruise et al. |
| 2002/0176893 A1 | 11/2002 | Wironen et al. |
| 2002/0183244 A1 | 12/2002 | Ollerenshaw et al. |
| 2002/0183838 A1 | 12/2002 | Liddicoat et al. |
| 2002/0188171 A1 | 12/2002 | Alferness et al. |
| 2003/0017150 A1 | 1/2003 | Torphy |
| 2003/0018318 A1 | 1/2003 | Melsky |
| 2003/0029452 A1 | 2/2003 | Suki et al. |
| 2003/0050648 A1 | 3/2003 | Alferness et al. |
| 2003/0051733 A1 | 3/2003 | Kotmel et al. |
| 2003/0055331 A1 | 3/2003 | Kotmel et al. |
| 2003/0064050 A1 | 4/2003 | Malik et al. |
| 2003/0069488 A1 | 4/2003 | Alferness et al. |
| 2003/0070676 A1 | 4/2003 | Cooper et al. |
| 2003/0070682 A1 | 4/2003 | Wilson et al. |
| 2003/0070683 A1 | 4/2003 | Deem et al. |
| 2003/0075170 A1 | 4/2003 | Deem et al. |
| 2003/0083671 A1 | 5/2003 | Rimbaugh et al. |
| 2003/0100921 A1 | 5/2003 | Addis et al. |
| 2003/0109866 A1 | 6/2003 | Edwards et al. |
| 2003/0113369 A1 | 6/2003 | Martin et al. |
| 2003/0127090 A1 | 7/2003 | Gifford et al. |
| 2003/0130657 A1 | 7/2003 | Tom et al. |
| 2003/0138481 A1 | 7/2003 | Zadi |
| 2003/0154988 A1 | 8/2003 | DeVore et al. |
| 2003/0158515 A1 | 8/2003 | Gonzalez et al. |
| 2003/0159700 A1 | 8/2003 | Laufer et al. |
| 2003/0181356 A1 | 9/2003 | Ingenito |
| 2003/0181922 A1 | 9/2003 | Alferness |
| 2003/0183235 A1 | 10/2003 | Rimbaugh et al. |
| 2003/0191496 A1 | 10/2003 | Edwards et al. |
| 2003/0194797 A1 | 10/2003 | Young et al. |
| 2003/0195385 A1 | 10/2003 | DeVore |
| 2003/0195511 A1 | 10/2003 | Barry |
| 2003/0199440 A1 | 10/2003 | Dack et al. |
| 2003/0212337 A1 | 11/2003 | Sirokman |
| 2003/0212412 A1 | 11/2003 | Dillard et al. |
| 2003/0216321 A1 | 11/2003 | Lawrence et al. |
| 2003/0224430 A1 | 12/2003 | Xiao |
| 2003/0232019 A1 | 12/2003 | Basu et al. |
| 2003/0232048 A1 | 12/2003 | Yang et al. |
| 2003/0233099 A1 | 12/2003 | Danaek et al. |
| 2004/0009122 A1 | 1/2004 | Klaveness et al. |
| 2004/0009217 A1 | 1/2004 | Martin et al. |
| 2004/0010209 A1 | 1/2004 | Sirokman |
| 2004/0010289 A1 | 1/2004 | Biggs et al. |
| 2004/0024356 A1 | 2/2004 | Tanaka |
| 2004/0030262 A1 | 2/2004 | Fisher et al. |
| 2004/0031494 A1 | 2/2004 | Danek et al. |
| 2004/0038868 A1 | 2/2004 | Ingenito |
| 2004/0040555 A1 | 3/2004 | Tanaka |
| 2004/0043407 A1 | 3/2004 | Chen et al. |
| 2004/0047855 A1 | 3/2004 | Ingenito |
| 2004/0048302 A1 | 3/2004 | Chen et al. |
| 2004/0049187 A1 | 3/2004 | Burnett et al. |
| 2004/0052850 A1 | 3/2004 | Schankereli |
| 2004/0055606 A1 | 3/2004 | Hendricksen et al. |
| 2004/0059263 A1 | 3/2004 | DeVore et al. |
| 2004/0063613 A1 | 4/2004 | Rolke et al. |
| 2004/0072756 A1 | 4/2004 | Wilkie et al. |
| 2004/0073155 A1 | 4/2004 | Laufer et al. |
| 2004/0073191 A1 | 4/2004 | Soltesz et al. |
| 2004/0073201 A1 | 4/2004 | Cooper et al. |
| 2004/0073241 A1 | 4/2004 | Barry et al. |
| 2004/0078054 A1 | 4/2004 | Biggs et al. |
| 2004/0081648 A1 | 4/2004 | Afeyan et al. |
| 2004/0081676 A1 | 4/2004 | Schankereli et al. |
| 2004/0086896 A1 | 5/2004 | Carman et al. |
| 2004/0087778 A1 | 5/2004 | Feige et al. |
| 2004/0106613 A1 | 6/2004 | Lu et al. |
| 2004/0120849 A1 | 6/2004 | Stewart et al. |
| 2004/0120979 A1 | 6/2004 | Roessler et al. |
| 2004/0121362 A1 | 6/2004 | Whitney et al. |
| 2004/0124185 A1 | 7/2004 | Patel et al. |
| 2004/0126777 A1 | 7/2004 | Bhatt et al. |
| 2004/0133168 A1 | 7/2004 | Salcudean et al. |
| 2004/0158228 A1 | 8/2004 | Perkins |
| 2004/0172058 A1 | 9/2004 | Edwards et al. |
| 2004/0176801 A1 | 9/2004 | Edwards et al. |
| 2004/0210248 A1 | 10/2004 | Gordon et al. |
| 2004/0211434 A1 | 10/2004 | Loomas et al. |
| 2004/0220556 A1 | 11/2004 | Cooper et al. |
| 2004/0225254 A1 | 11/2004 | Tanaka et al. |
| 2004/0231674 A1 | 11/2004 | Tanaka |
| 2004/0234575 A1 | 11/2004 | Horres et al. |
| 2004/0237966 A1 | 12/2004 | Tanaka |
| 2004/0244802 A1 | 12/2004 | Tanaka |
| 2004/0244803 A1 | 12/2004 | Tanaka |
| 2005/0004599 A1 | 1/2005 | McNally-Heintzelman et al. |
| 2005/0015106 A1 | 1/2005 | Perkins et al. |
| 2005/0043751 A1 | 2/2005 | Phan et al. |
| 2005/0043752 A1 | 2/2005 | Phan et al. |
| 2005/0049615 A1 | 3/2005 | Cooper et al. |
| 2005/0060041 A1 | 3/2005 | Phan et al. |
| 2005/0060042 A1 | 3/2005 | Phan et al. |
| 2005/0061322 A1 | 3/2005 | Freitag |
| 2005/0085801 A1 | 4/2005 | Cooper et al. |
| 2005/0096529 A1 | 5/2005 | Cooper et al. |
| 2005/0107783 A1 | 5/2005 | Tom et al. |
| 2005/0119614 A1 | 6/2005 | Mesky |
| 2005/0281739 A1 | 12/2005 | Gong et al. |
| 2005/0281740 A1 | 12/2005 | Gong et al. |
| 2005/0281796 A1 | 12/2005 | Gong et al. |
| 2005/0281797 A1 | 12/2005 | Gong et al. |
| 2005/0281798 A1 | 12/2005 | Gong et al. |
| 2005/0281799 A1 | 12/2005 | Gong et al. |

| | | | |
|---|---|---|---|
| 2005/0281800 A1 | 12/2005 | Gong et al. | |
| 2005/0281801 A1 | 12/2005 | Gong et al. | |
| 2005/0281802 A1 | 12/2005 | Gong et al. | |
| 2005/0282748 A1 | 12/2005 | Gong et al. | |
| 2005/0288549 A1 | 12/2005 | Mathis | |
| 2005/0288550 A1 | 12/2005 | Mathis | |
| 2005/0288684 A1 | 12/2005 | Aronson et al. | |
| 2005/0288702 A1 | 12/2005 | McGurk et al. | |
| 2006/0004400 A1 | 1/2006 | McGurk et al. | |
| 2006/0009748 A1 | 1/2006 | Mathis | |
| 2006/0025815 A1 | 2/2006 | McGurk et al. | |
| 2006/0167416 A1 | 7/2006 | Mathis et al. | |
| 2007/0221230 A1 | 9/2007 | Thompson et al. | |

FOREIGN PATENT DOCUMENTS

| | | | |
|---|---|---|---|
| EP | 0529719 A1 | 3/1993 | |
| EP | 1070049 B1 | 1/2001 | |
| EP | 1378518 A1 | 1/2004 | |
| EP | 1433486 A1 | 6/2004 | |
| FR | 2840796 | 12/2003 | |
| GB | 2324729 B | 1/2002 | |
| WO | WO 96/10418 A1 | 4/1996 | |
| WO | WO 99/64446 A1 | 12/1999 | |
| WO | WO 00/13592 A1 | 3/2000 | |
| WO | WO 00/17227 A1 | 3/2000 | |
| WO | WO 01/13839 A1 | 3/2001 | |
| WO | WO 02/00270 A1 | 1/2002 | |
| WO | WO 02/00275 A1 | 1/2002 | |
| WO | WO 02/02158 A1 | 1/2002 | |
| WO | WO 02/072751 A2 | 9/2002 | |
| WO | WO 02/072769 A2 | 9/2002 | |
| WO | WO 02/072788 A2 | 9/2002 | |
| WO | WO 03/010327 A2 | 2/2003 | |
| WO | WO 03/064639 A1 | 8/2003 | |
| WO | WO 03/077768 A1 | 9/2003 | |
| WO | WO 03/090682 A2 | 11/2003 | |
| WO | WO 2004/001060 A2 | 12/2003 | |
| WO | WO 2004/020620 A1 | 3/2004 | |
| WO | WO 2004/031235 A1 | 4/2004 | |
| WO | WO 2004/031253 A1 | 4/2004 | |
| WO | WO 2004/045634 A1 | 6/2004 | |
| WO | WO 2004/052236 A2 | 6/2004 | |
| WO | WO 2004/053117 A2 | 6/2004 | |
| WO | WO 2004/054556 A1 | 7/2004 | |
| WO | WO 2004/062505 A1 | 7/2004 | |
| WO | WO 2004/086977 A1 | 10/2004 | |

OTHER PUBLICATIONS

Nakamura et al., Japanese Journal of medicine 26, 319-322 (1987).*
Takayama et al., "A new technique of thoracoscopic pleurodesis for refractory hepatic hydrothorax," *Surgical Endoscopy*, vol. 18, No. 1, Jan. 2004, pp. 140-143.
International Search Report and Written Opinion of PCT Application No. PCT/US05/24172, dated Jun. 5, 2008, 11 page total.
Belorgey, Didier et al. 1998. Effect of polynucleotides on the inhibition of neutrophil elastase by mucus proteinase inhibitor and $a_1$-proteinase inhibitor. *Biochemistry* 37(46): 16416-16422.
Chambers, Rachel C. et al. 1998. Cadmium inhibits proteoglycan and procollagen production by cultured human lung fibroblasts. *American Journal of Respiratory Cell and Molecular Biology* 19: 498-506.
Cho, Raymond J. et al. 1998. Parallel analysis of genetic selections using whole genome oligonucleotide arrays. *Proceedings of the National Academy of Sciences of the United States of America*, 95: 3752-3757.
Covault, H. Patrick et al. 1982. Liquid-chromatographic measurement of elastin. *Clinical Chemistry* 28(7): 1465-1468.
Cuvelier, A. et al. 2000. Inter-alpha tripsin inhibitor (ITI) proteins: an important role in the extracellular matrix *Rev. Mal. Respir.* 17: 437-446.
De Roos, Albert et al. 1991. Myocardial infarct sizing and assessment of reperfusion by magnetic resonance imaging: a review *International Journal of Cardiac Imaging* 7(2): 133-138.

Duranton, Jerome et al. 2003. Inhibition of proteinase 3 by $a_1$-antitrypsin in vitro predicts very fast inhibition in vivo. *American Journal of Respiratory Cell and Molecular Biology* 29: 57-61.
Eng, Jibah et al. 1990. Successful closure of bronchopleural fistula with adhesive tissue. *Scand J Thor Cardiovasc Surg* 24(2): 157-59.
Felici, Franco et al. 1991. Selection of antibody ligands from a large library of oligopeptides expressed on a multivalent exposition vector. *Journal of Molecular Biology* 222(1): 301-310.
Francis, Gillian E. 1992. Protein modification and fusion proteins. *Focus on Growth Factors* 3: 4-10, Royal Free Hospital School of Medicine, London, UK.
Fromont-Racine, Micheline et al. 1997. Toward a functional analysis of the yeast genome through exhaustive two-hybrid screens. *Nature Genetics* 16: 277-282.
Fujiwara, Yasuyuki. 2004. Cell biological study on abnormal proteoglycan synthesis in vascular cells exposed to heavy metals. *Journal of Health Science* 50(3): 197-204.
Gennaro, A.R. (Edit.) 1985. *Remington's Pharmaceutical Sciences*. Easton: Mack Printing Company.
Harper, J. Wade et al. 1993. The p21 cdk-interacting protein cip1 is a potent inhibitor of G1 cyclin-dependent kinases. *Cell* 75(4): 805-816.
Hermanson, Greg T. 1996. *Bioconjugate Techniques*. San Diego: Academic Press, Inc.
Inaspettato, G. et al. 1994. Endoscopic treatment of bronchopleural fistulas using n-butyl-2-cyanoacrylate. *Surgical Laparoscopy & Endoscopy* 4(1): 62-64.
Ingenito, Edward P. et al. 2001. Brochoscopic volume reduction: a safe and effective alternative to surgical therapy for emphysema. *American Journal of Respiratory and Critical Care Medicine* 164: 295-301.
Ingenito, Edward P. et al. 2003. Bronchoscopic lung volume reduction using tissue engineering principles. *American Journal of Respiratory and Critical Care Medicine* 167: 771-778.
Irving, James A. et al. 2000. Phylogeny of the serpin superfamily: implications of patterns of amino acid conservation for structure and function. *Genome Research* 10(12): 1845-1864.
Ito, Satoru et al. 2004. Tissue heterogeneity in the mouse lung: effects of elastase treatment. *Journal of Applied Physiology* 97(1): 204-212. available as an APS Article in PresS Mar. 12, 2004.
Janoff, Aaron. 1985. State of the art: elastases and emphysema—current assessment of the protease-antiprotease hypothesis. *American Review of Respiratory Disease* 132(2): 417-433.
Lam, K.N. Sin Fai et al. 1998. X-Ray Diagnosis: A Physician's Approach. Singapore: Springer.
Laurell, C.B. et al. 1963. The electrophoretic $a_1$-globulin pattern of serum in $a_1$-antitrypsin deficiency. *Scandinavian Journal of Clinical and Laboratory Investigation* 15: 132-140.
Menache, M.G. et al. 1995. Particle inhalability curves for humans and small laboratory animals. *The Annals of Occupational Hygiene* 39(3): 317-328.
Oldenburg, Kevin R. et al. 1992. Peptide ligands for a sugar-binding protein isolated from a random peptide library. *Proceedings of the National Academy of Sciences of the United States of America* 89(12): 5393-5397.
Osakabe, Toni et al. 1995. Comparison of ELISA and HPLC for the determination of desmosine or isodesmosine in aortic tissue elastin. *Journal of Clinical Laboratory Analysis* 9(5): 293-296.
Parmley, Stephen F. et al. 1988. Antibody-selectable filamentous fd phage vectors: affinity purification of target genes. *Gene*, 73(2): 305-318.
Powers, William J. et al. 1982. Indium-111 platelet scintigraphy in cerebrovascular disease. *Neurology* 32: 938-943.
Raabe, Otto G. 1982. Comparison of the criteria for sampling 'inhalable' and 'respirable' aerosols. *Ann. Occup. Hyg.* 26(1-4): 33-45.
Raabe, Otto G. et al. 1982. Studies of the chronic inhalation of coal fly ash by rats. *Ann. Occup. Hyg.* 26(1-4): 189-211.
Rajotte, Daniel et al. 1999. Membrane dipeptidase is the receptor for a lung-targeting peptide identified by in vivo phaqe display. *The Journal of Biological Chemistry* 274(17): 11593-11598.
Rowe, Raymond C., et al. 2003. *Handbook of Pharmaceutical Excipients* 4th Edition. London: Pharmaceutical Press.

Senior, Robert M. et al. 1988. Chapter 74: the pathogenesis of emphysema. *Pulmonary Diseases and Disorders*, Second Edition, 2: 1209-1218. New York: McGraw-Hill Book Company.

Sifers, Richard N. et al. 1989. Genetic control of human alpha-1-antitrypsin. *Molecular Biology and Medicin* 6: 127-135.

Slone, Richard M. et al. 2000. Body CT: A Practical Approach. New York: McGraw-Hill.

Starcher, Barry C. 2000. Lung elastin and matrix. *Chest* 117(5): 229S-234S.

Starcher, Barry et al. 1995. A role for neutrophil elastase in the progression of solar elastosis. *Connective Tissue Research* 31(2): 133-140.

Stone, Phillip J. et al. 1991. Measurement of urinary desmosine by isotope dilution and high performance liquid chromatography. *American Review of Respiratory Disease* 144(2): 284-290.

Stout, George H. et al. 1989. X-Ray Structure Determination: A Practical Guide, 2nd Edition. New York: John Wiley & Sons.

Suki, Bela et al. 2003. On the progressive nature of emphysema. *American Journal of Respiratory and Critical Care Medicine* 168: 516-521.

Swanson, Scott J. et al. 1997. No-cut thoracoscopic lung plication: a new technique for lung volume reduction surgery. *Journal of the American College of Surgeons* 185(1): 25-32.

Thakur, Mathew L. et al. 1976. Indium-III labeled platelets: studies on preparation and evaluation of in vitro and in vivo functions. *Thrombosis Research* 9: 345-357.

The United States Pharmacopeia, 29th Revision. 2006. The United States Pharmacopeial Convention.

Valadon, Philippe. et al. 1996. Peptide libraries define the fine specificity of anti-polysaccharide antibodies to *Cryptococcus neoformans*. *J. Mol. Biol.* 261: 11-22.

Westerink, M.A. Julie et al. 1995. Peptide mimicry of the meningococcal group C capsular polysaccharide. *Proceedings of the National Academy of Sciences of the United States of America* 92(9): 4021-4025.

Wong, Shan S. 1991. *Chemistry of Protein Conjugation and Cross-Linking*. Boca Raton: CRC Press, Inc.

Zimmerman, Morris et al. 1989. Chapter 12: design and properties of synthetic elastase inhibitors. *Elastin and Elastases* 2: 109-123. Boca Raton: CRC Press, Inc.

Mathis, M., U.S. Appl. No. 11/286,445 entitled "Steerable Device for Accessing a Target Site and Methods", filed Nov. 23, 2005.

McGurk, E. et al., U.S. Appl. No. 11/178,243 entitled "Lung Device With Sealing Features", filed Jul. 8, 2005.

Moser, et al. Biologic half-life and organ distribution of radiolabeled human PiM and PiZ alpha-1-antitrypsin in the dog. J Lab Clin Med. 1978; 91(2):214-22.

Moser, et al. Intravenous administration of alpha-l-proteinase inhibitor in patients of PiZ and PiM phenotype. Preliminary report. Am J Med. 1988; 84(6A):70-4.

"Chest Tube Insertion"—Encyclopedia of Surgery: A Guide for Patients and Caregivers; retrieved from the Internet: <<http://www.surgeryencyclopedia.com/Ce-Fi/Chest-Tube-Insertion.html>>, 6 pages total.

Cook Medical Incorporated, "Thal-Quick Chest Tube—Sets and Trays" [pamphlet], 2005; retrieved from the Internet: <<http://www.cookmedical.com/cc/content/mmedia/C-TQTS505.pdf>>, 8 pages total.

"Percutaneous"—Wikipedia; retrieved from the Internet: <<http://en.wikipedia.org/wiki/Percutaneous >>, 1 page total.

"What Size Chest Tube?"—Medscape; retrieved from the Internet: <<http//www.medscape.com/viewarticle/460441_2>>, 3 pages total.

* cited by examiner

PLEURAL EFFUSION TREATMENT DEVICE, METHOD AND MATERIAL

CROSS-REFERENCE

This application claims the benefit of U.S. Provisional Application No. 60/586,887, filed Jul. 8, 2004, which is incorporated herein by reference in its entirety.

BACKGROUND OF THE INVENTION

1. Field of the Invention

The invention relates generally to methods, devices and materials for use in treating pleural effusion.

2. Description of the Related Art

In the thoracic cavity, a layer of visceral pleura covers the surface of the lung, and a layer of parietal pleura lines the inner surface of the thoracic cavity, including the inside of the ribs and diaphragm. These smooth membranes normally contain a small amount of clear, plasma-like pleural fluid that helps reduce the friction between the lung surface and its surroundings as the lung expands and contracts with respiration. The accumulation of an abnormal amount of fluid between the visceral and parietal pleuras is called pleural effusion. For example, a patient with lung cancer can have a plurality of parietal or visceral lesions that produce clear fluid that gets into the pleural space.

The etiology of pleural effusions is varied and includes congestive heart failure, pneumonia, and pulmonary malignancies among others. Patients with pleural effusion often present with dyspnea, minimal to moderate chest pain, dullness on percussion and possible pleural friction rub and/or mediastinal shift. The existence of an effusion can generally be confirmed with chest radiography or CT. There is significant potential for morbidity and mortality due to the tendency for the volume of the pleural effusion fluid to compress the lungs, thereby restricting their expansion.

If the pleural effusion is recurring or is caused by a progressive pulmonary malignancy, pleurodesis is generally indicated. Pleurodesis is a therapeutic procedure involving drainage of the pleural fluid and introduction of a sclerosing agent between the two pleural membranes to cause a scarring reaction, which effectively fuses the two layers to one another. The goal is to close the pleural space and preclude fluid from entering it again. See, e.g., U.S. Pat. No. 5,484,401, which describes some prior treatments for pleural effusion. Current treatments include, for example, surgical intervention to drain the fluid, distribute talc into the pleural space, draw a vacuum, and then monitor the patient in the hospital.

A variety of agents are currently used to perform chemical pleurodesis, including radioactive isotopes, tetracycline, chemotherapeutic agents and talc. Two things are necessary for a successful pleurodesis: (1) The sclerosing agent must be evenly distributed across the pleural surfaces; and (2) the lung must still be able to expand effectively after the procedure.

Treatment for pleural effusion currently involves introduction of a chest tube through the chest wall into the pleural space, followed by drainage of the fluid. The chest tube is then clamped, allowing the lung to partially collapse. A syringe containing a sclerosing agent is attached to the chest tube, and the agent is insufflated into the pleural space. The chest tube is unclamped, allowing the lung to inflate fully and to pull the agent further into the pleural space. The patient is rotated in bed over the following few hours to assist in the equal distribution of the agent. The chest tube is removed when there is less than 100 cm$^3$ of fluid per day removed from the pleural space. This pleurodesis procedure may be done at the bedside.

The sclerosing agents irritate the pleural membranes, eventually causing them to become inflamed and scarred, which fuses the layers together. Talc is the most commonly used sclerosing agent and has a reported 90% success rate. Although talc has demonstrated a high rate of success, there are complications associated with the procedure, most of which are caused by the sclerosing agent and the nature of its action. Patients commonly experience pain during the installation of the agent, which is very irritating and inflammatory, and a narcotic is therefore usually administered prior to the procedure. Also, fever is common in more than 30% of patients undergoing talc pleurodesis, possibly due to the pleuritis it causes. The fever generally lasts for approximately 48 hours.

It is difficult to evenly distribute most sclerosing agents, especially talc, because they do not flow. Talc does not mix well with saline and has a tendency to clump. Incomplete lung expansion due to a partially trapped lung can occur when pleurodesis is only partially successful.

Additionally, pleurodesis is performed over several days. While waiting for the full effects of the scarring action to take place, the patient is in danger of partial or full respiratory failure. Thus, hospitalization and close monitoring is required during this period.

What is needed, therefore, is a device for distributing sclerosing agents which reduces the risk of partial or full respiratory failure.

SUMMARY OF THE INVENTION

The present invention provides methods, materials and devices for treating pleural effusions. Other methods and compositions are also provided in U.S. patent applications entitled "Lung Device with Sealing Features" application Ser. No. 11/178,243 filed Jul. 8, 2005; "Intra-Bronchial Lung Volume Reduction System," application Ser. No. 11/153,235 filed Jun. 14, 2005; "Targeting Damaged Lung Tissue Using Compositions," application Ser. No. 11/008,577, filed Dec. 8, 2004; "Targeting Damaged Lung Tissue," application Ser. No. 11/008,092, filed Dec. 8, 2004; "Targeting Sites of Damaged Lung Tissue Using Composition," application Ser. No. 11/008,094 filed Dec. 8, 2004; "Targeting Sites of Damaged Lung Tissue," application Ser. No. 11/008,578, filed Dec. 8, 2004; "Imaging Damaged Lung Tissue Using Compositions," application Ser. No. 11/008,649, filed Dec. 8, 2004; "Imaging Damaged Lung Tissue," application Ser. No. 11/008,777, filed Dec. 8, 2004; "Lung Volume Reduction Using Glue Compositions," application Ser. No. 11/008,093, filed Dec. 8, 2004; "Glue Composition for Lung Volume Reduction," application Ser. No. 11/008,087 filed Dec. 8, 2004; "Glue Composition for Lung Volume Reduction," application Ser. No. 11/008,580 filed Dec. 8, 2004; and "Lung Volume Reduction Using Glue Composition," application Ser. No. 11/008,782 filed Dec. 8, 2004.

One aspect of the invention provides a method of treating a patient for pleural effusion comprising percutaneously delivering an adhesive material to a pleural space of the patient. The delivering step can also comprise ejecting the adhesive material from a delivery device into the pleural space and further comprising mixing components of the adhesive material in the delivery device prior to the ejecting step. In some embodiments, while performing the method of the invention, the delivery device converts from a delivery configuration to an operational configuration. A further embodiment of the method can include percutaneously inserting a pleural space access member into the patient. Suction can be applied to the pleural space prior to delivering the adhesive material to the pleural space in performing the method of an embodiment of the invention. When suction is applied, the suction can be applied through the pleural space access member. Further, the delivering step of the method can comprise delivering the adhesive material through the pleural space access member. An embodiment of the method can also include delivering adhesive material to the pleural space without delivering a fibrosis inducing material to the pleural space. The adhesive material can be spread within the pleural space. The adhesive materials suitable for any of the embodiments of the methods of the invention have strength values up to 1.5 psi, or more; preferably having a strength value between 0.2-0.6 psi. In addition, the adhesive material suitable for any of the embodiments of the methods of the invention have viscosity levels of 1.1 centipoise and higher. Further, materials suitable for performing any of the methods of the invention can be selected from the group comprising hydrogels, proteins, polymers and cross-linking agents. The hydrogel adhesive may include material selected from the group consisting of hyalurons, hyaluronic acid, alginates, chitins, chitosans, and derivatives thereof. The protein material comprises material that can be selected from the group consisting of albumins, porcine albumin, collagens and gelatins. The polymer material comprises material selected from the group consisting of poly(lactic acid) and poly(glycolide). The cross-linking agent material comprises material that may be selected from the group consisting of glutaraldehyde and stable polyaldehyde.

Another aspect of the invention includes a pleural effusion treatment apparatus comprising an adhesive material adapted to adhere pleural membranes defining a pleural space and a pleural space access member adapted to deliver the adhesive material to the pleural space. In an embodiment of the apparatus, the pleural space access member comprises an adhesive material delivery device. Further, the adhesive material delivery device can comprise a syringe. Adhesive materials suitable for the embodiments of the invention comprise two or more components, the delivery device comprising a mixing element adapted to mix the two components prior to injection of the adhesive material into the patient. The pleural space access member of an embodiment of the invention can comprise a chest tube. Additionally, an apparatus of the invention can comprise a suction apparatus. Where a suction apparatus is provided, the apparatus can be adapted to apply suction through the pleural space access member. A spreading element can also be provided that is adapted to spread adhesive material within the pleural space. For example, the pleural space access member can be a catheter. Various shapes of the pleural space access member can be employed including, but not limited to, a loop, an S shape, a V shape. Additionally, the shape can have an actuator forming a bend, a pull wire, and/or a memory element incorporated therein. Further, materials suitable for use in the adhesives suitable for the apparatus of the embodiments of the invention can be selected from the group comprising hydrogels, protein, and cross-linking agents. Polymer such as poly(lactic acid), poly(glycolide) can also be provided.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
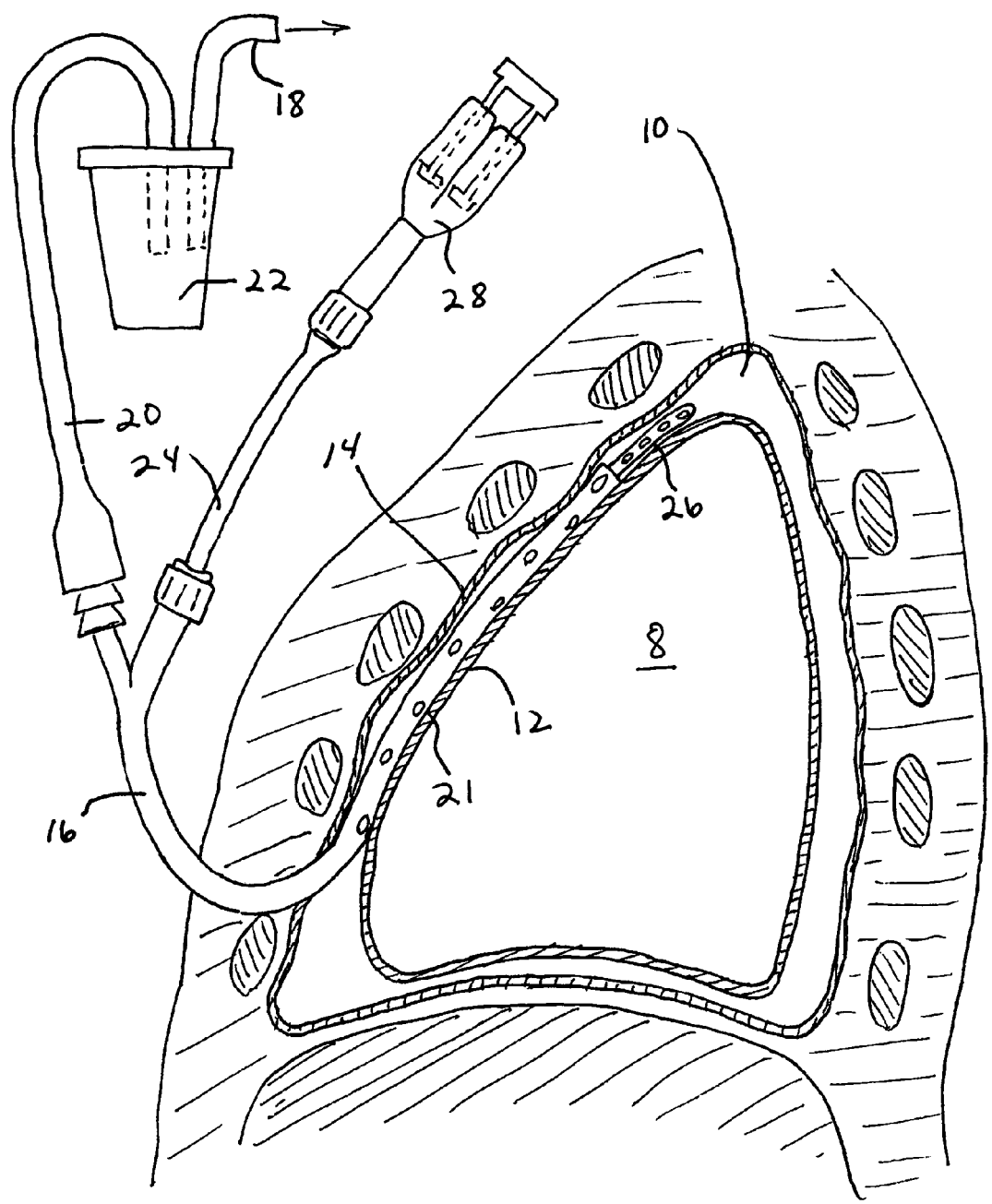
FIG. 1 shows a lateral cross-sectional view of a lung and chest cavity of a patient showing a device according to one embodiment of the invention.

The invention provides methods, materials and devices for treating a pleural effusion by gluing the pleura together using a suitable adhesive, such as glue, as a sealant to prevent the passage of liquid or gas. The materials used in the method include a fast-acting adhesive that cures in less than three days, more preferably less than two days, even more preferably less than one day, and most preferably less than one hour. A specific cure time may be tunable to allow for glue distribution before curing fully. Some glue formulations may require ancillary light sources, primers, catalysts, radiofrequency energy, electrical energy or radiation to cause the glue to cure.

Glue formulations for use with this invention may include solids, semi-solids, hydrogels, foams, agars, or sol-gels. Some glue formulations work in wet or dry tissue surface conditions. Some glue formulations may also stop active bleeding (i.e., provide hemostasis). The glues are preferably biocompatible and can successfully fuse tissue in wet conditions. The glues adhere the pleura without causing fibrosis, inflammation or scarring of the pleural tissue. The glues are flexible and conformable to tissue geometry, and they possess high tensile strength. Solvents can be used to deliver the glue in order to drive the glue into the tissue.

One preferred embodiment is a glue formulation that crosslinks (chemically bonds) to the biological tissue it is applied to. More specifically, the adhesive either crosslinks to collagen or promotes the crosslinking of collagen at two adjoining tissue surfaces to be fused and allow for high adhesion.

Another preferred embodiment is a glue formulation that has a radiopaque component so that the glued boundary can be identified using x-ray-based imaging techniques during or after the procedure. Additives may include tantalum, platinum, bismuth, radiopaque metals, and polymers. Polymers can include, for example, poly(lactic acid) and poly(glycolide). Agents and drugs can also be added as primers.

Although many alternative glue formulations may be suitable to achieve these goals, one preferred glue formulation consists of a combination of a cross-linking agent, such as glutaraldehyde or stable polyaldehyde, and a protein, such as albumin, including porcine albumin and collagen, with or without additional additives. One such material suitable for pleural fusion is described in US Patent Application Publ. No. 2004/0081676. It works uniquely as a biologic glue that typically cures within a few minutes to fuse pleural layers without causing or requiring inflammation or heat. The glue's intrinsic viscosity can be tuned to allow for fast or slow spreading across target lung regions. The glue may be used for other purposes as well, such as anastomosis of blood vessels and bronchi/bronchioles and to seal pulmonary structures from air leaks, bleeding, or fluid leaks. Another adhesive that may be suitable is a cyanoacrylate adhesive.

Alternative glue formulations may be suitable to achieve these goals such as a combination of any one of the previously described components in combination with other additives that may include elastin, fibrin, glycoprotein, liposomes, thrombin, calcium, neuroleptics, vitamins, growth factors, glucocorticosteroids, steroids, antibiotics, antibacterial compounds, bacteriocidal and bacteriostatic compounds, antiviral compounds, antifungal compounds, antiparasitic compounds, tumoricidal compounds, tumoristatic compounds, toxins, enzymes, enzyme inhibitors, proteins, peptides, minerals, neurotransmitters, lipoproteins, glycoproteins, immunomodulators, immunoglobulins and fragments thereof, dyes, radiolabels, radiopaque compounds, fluorescent compounds, fatty acids, polysaccharides, cell receptor binding molecules, anti-inflammatories, antiglaucomic compounds, mydriatic compounds, anesthetics, nucleic acids, and polynucleotides.

The glue can be packaged sterile, in a single part or in two liquid parts in an applicator. Upon delivery of a two-part formulation, liquid components can be mixed as they are delivered, by an applicator or stirring or mixing nozzle device. After application, the formulation may quickly or slowly solidify into a flexible solid glue. The glue can also be premixed and then applied. The glue may be formulated as a two part solution that can be applied independently. In doing so, the first part may be applied and allowed for spread time before the second is applied.

Devices for use with the invention preferably introduce or spread the glue evenly over the surfaces of the visceral and parietal pleurae. The pleural effusion glue may be applied in an aerosol form to cover large organ surfaces more effectively or as a liquid, via a syringe, a catheter (e.g., through the patient's chest tube), or other applicator.

FIG. 1 shows a lateral cross-sectional view of a patient's chest cavity. The pleural space 10 of lung 8 is defined by the visceral pleura 12 and the parietal pleura 14. A chest tube 16 has been inserted percutaneously into the pleural space. Suction applied from a suction source 18 may be used to draw excess fluid from the pleural space through holes 21 in chest tube 16 to suction line 20 and into fluid container 22.

A delivery catheter 24 having a plurality of holes 26 at its distal end is inserted through chest tube 16 into the pleural space. A two-part syringe 28 may be used to deliver an adhesive material through delivery catheter 24 into the pleural space. As described above, the adhesive material is preferably a glue that does not contain any fibrosis-inducing or inflammatory material. Curing of the glue causes pleurae 14 and 12 to adhere, thereby reducing the likelihood that the pleural space will again be filled with excess fluid.

Figure 2:
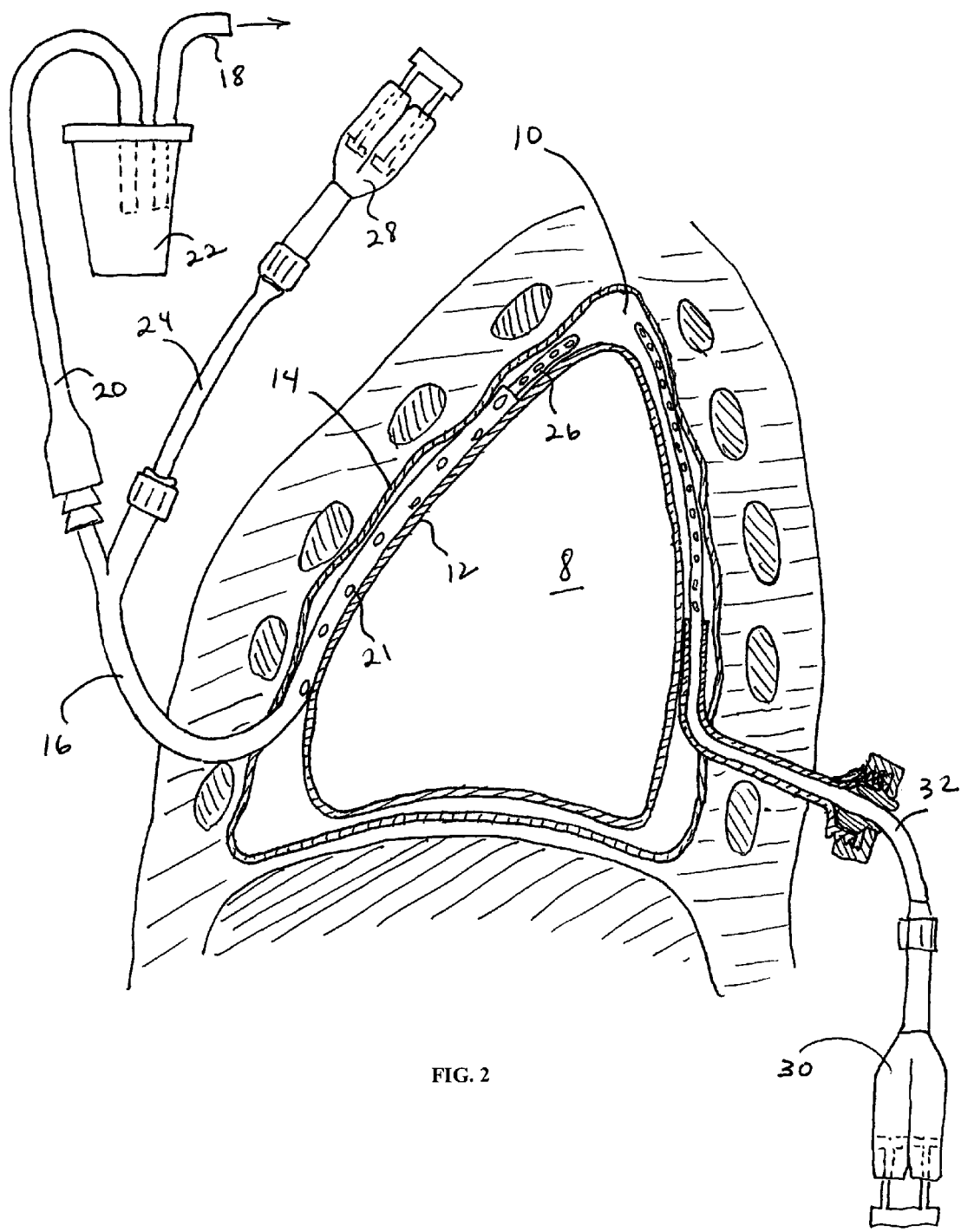
FIG. 2 shows a lateral cross-sectional view of a lung and chest cavity of a patient showing a device according to another embodiment of the invention.
Figure 3:
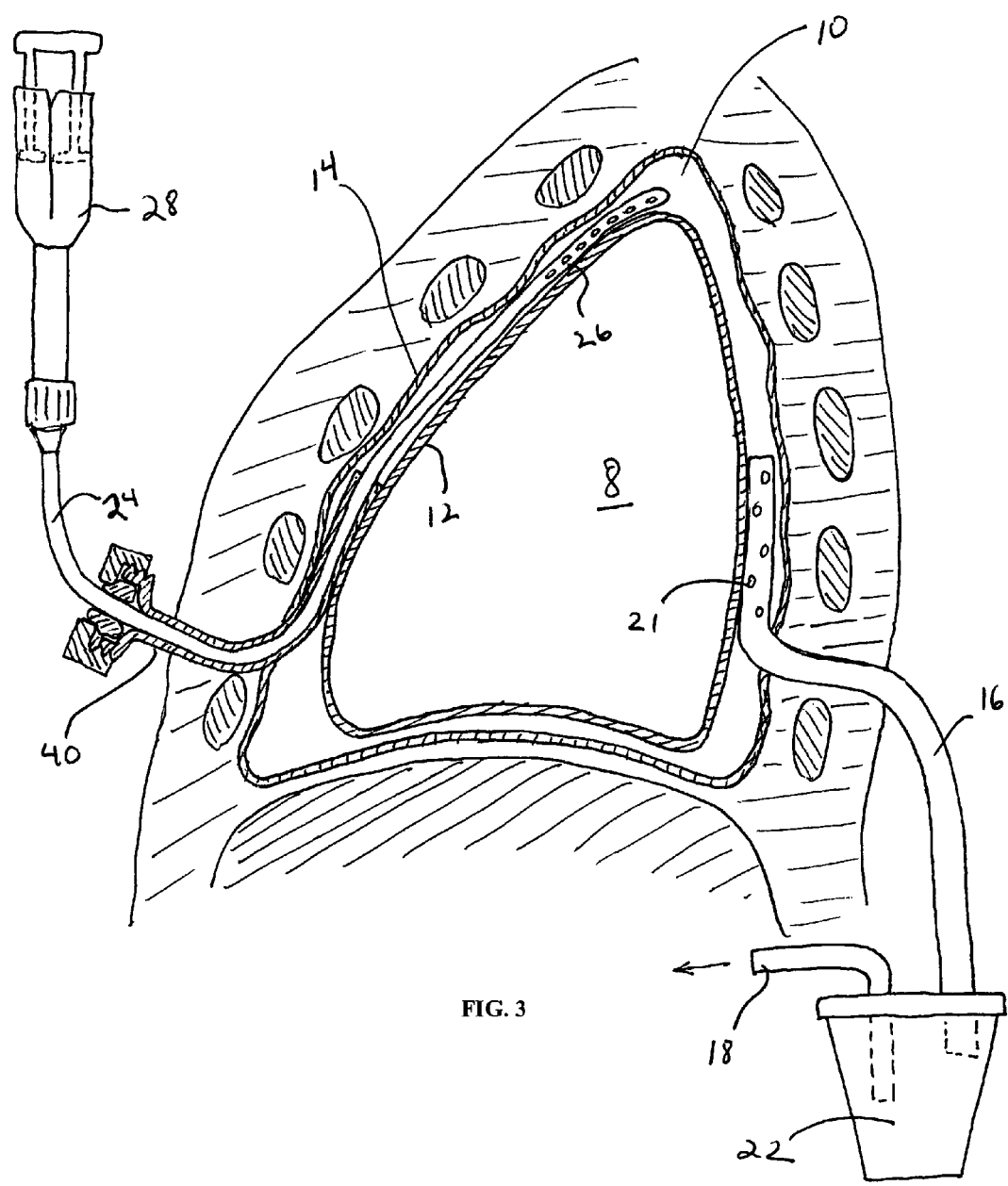
FIG. 3 shows a lateral cross-sectional view of a lung and chest cavity of a patient showing a device according to yet another embodiment of the invention.
Figure 4:
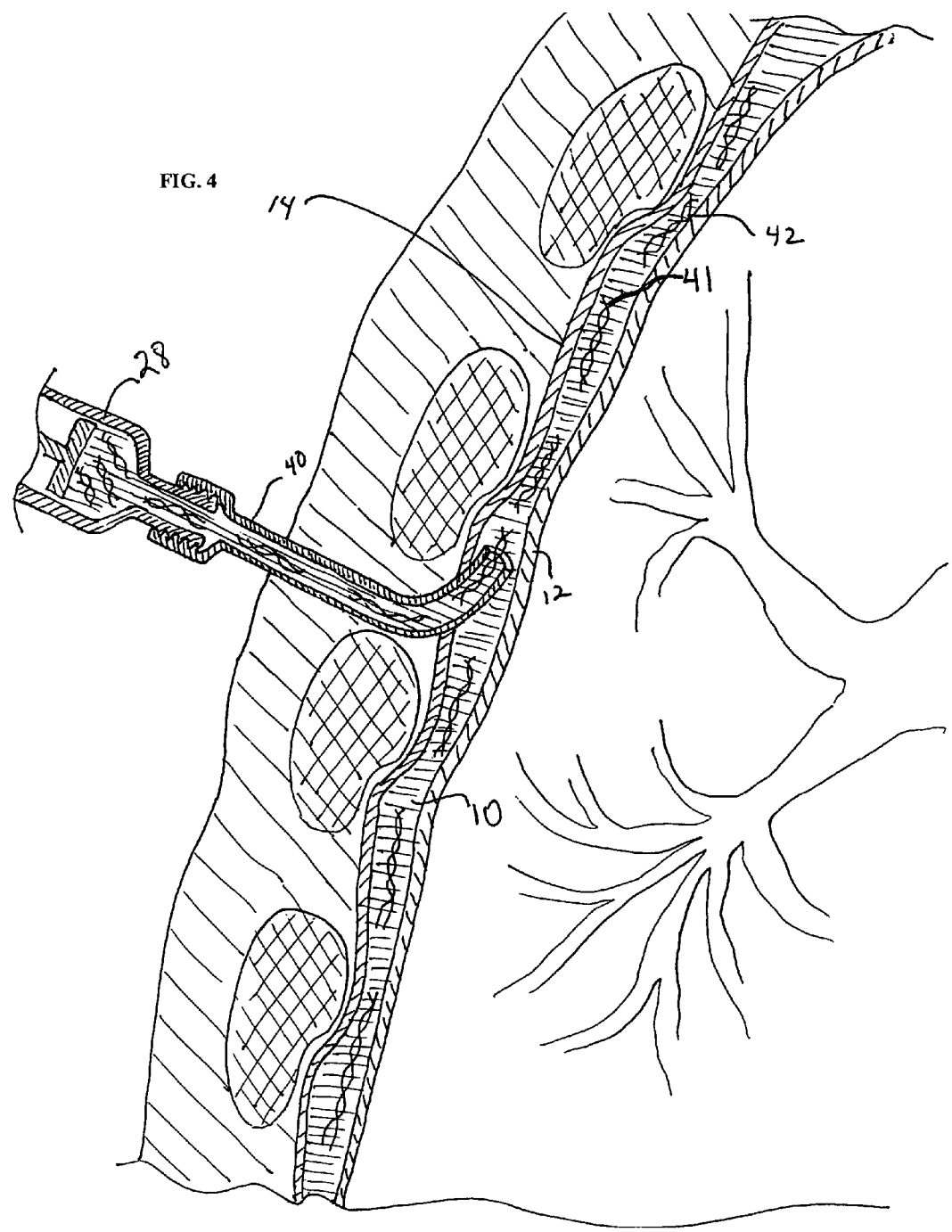
FIG. 4 shows a lateral cross-sectional view of a lung and chest cavity of a patient showing a device according to yet another embodiment of the invention having fiber reinforcement.

To ensure adequate adhesion of the pleurae, more than one device may be used to introduce adhesive material to the pleural space. For example, a second syringe 30 and delivery catheter 32 may be used together with the device of FIG. 1, as shown in FIG. 2. Alternatively, a separate chest tube 40 may be used for the adhesive delivery catheter 24, as shown in FIG. 3. The glue 42 preferably spreads over substantially all of the pleural space 10, as shown in FIG. 4. The glue 42 also includes a fiber reinforcement component 41 which creates a composite of glue and fiber. Fiber reinforcement can include short or long fibers, glass, polymer, ceramic, metallic, and other suitable materials, as would be appreciated by those of skill in the art. The fiber acts as reinforcement and the sealant acts as a matrix material in the composite. This is beneficial where distances between surfaces, or gaps, is large.

Figure 5:
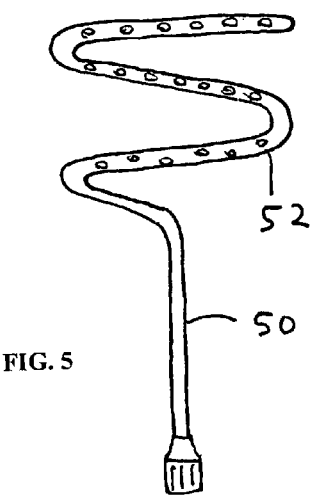
FIG. 5 shows an embodiment of an adhesive delivery catheter according to an embodiment of the invention.

FIGS. 5-9 show alternative embodiments of adhesive delivery catheters for use with the invention. In FIG. 5, delivery catheter 50 has one or more bends so that the catheter forms an S shape; In this embodiment, the shape shown in FIG. 5 is the catheter's operational configuration. Prior to use, catheter 50 is preferably straightened to a delivery configuration and inserted percutaneously through a chest tube into a patient's pleural space, then allowed to form (or is caused to form) its operational configuration. Holes 52 in catheter 50 permit the delivery of glue or other adhesive under pressure, such as from a syringe. The shape of the catheter and distribution of the holes help ensure even distribution of the adhesive material. In addition, the catheter may be moved within the pleural space after introduction of the adhesive material to rake or spread the material within the pleural space. Catheter 50 is returned to its delivery configuration for removal from the patient.

Figure 6:
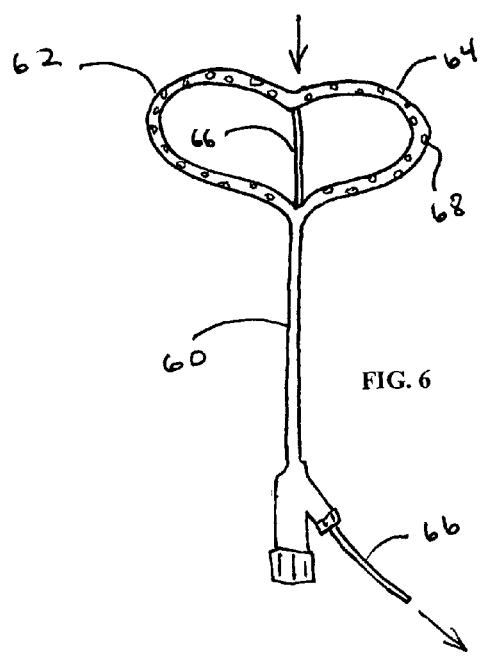
FIG. 6 shows an embodiment of an adhesive delivery catheter according to another embodiment of the invention.

FIG. 6 shows a delivery catheter 60 in an operational configuration in which the catheter has two branches 62 and 64 which split and meet to form an oval or heart shape. Catheter 60 may be straightened to a delivery configuration by moving branches 62 and 64 together for percutaneous delivery, then moved to its operational configuration by moving a pull wire or other actuator 66. As in the other embodiments, holes 68 in catheter 60 permit the delivery of glue or other adhesive under pressure, such as from a syringe. The shape of the catheter and distribution of the holes help ensure even distribution of the adhesive material. In addition, the catheter may be moved within the pleural space after introduction of the adhesive material to rake or spread the material within the pleural space. Catheter 60 is returned to its delivery configuration by actuator 66 for removal from the patient.

Figure 7:
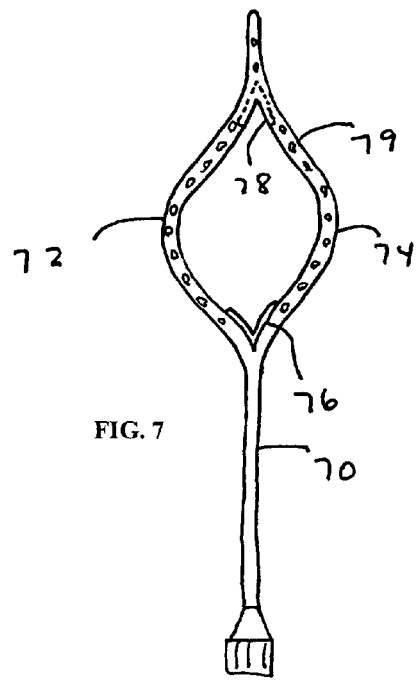
FIG. 7 shows an embodiment of an adhesive delivery catheter according to another embodiment of the invention.

FIG. 7 shows a delivery catheter 70 with two branches 72 and 74 separated into an operational configuration by spring elements 76 and 78 (made, e.g., from Nitinol or some other shape memory material). Catheter 70 may be straightened to a delivery configuration by moving branches 72 and 74 together against the action of the spring elements, then allowed to assume its operational configuration once inside the pleural space. Holes 79 in catheter 70 permit the delivery of glue or other adhesive under pressure, such as from a syringe. As in other embodiments, the shape of the catheter and distribution of the holes help ensure even distribution of the adhesive material. In addition, the catheter may be moved within the pleural space after introduction of the adhesive material to rake or spread the material within the pleural space. Catheter 70 is returned to its delivery configuration for removal from the patient, such as by inward camming action caused by pulling catheter 70 back into the distal end of a chest tube.

Figure 8:
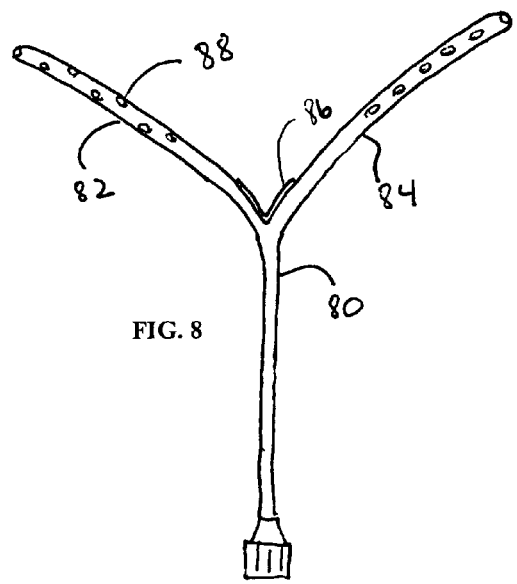
FIG. 8 shows yet another embodiment of an adhesive delivery catheter according to an embodiment of the invention.

FIG. 8 shows a delivery catheter 80 with two branches 82 and 84 separated into an operational configuration by a spring element 86. Catheter 80 may be straightened to a delivery configuration by moving branches 82 and 84 together against the action of the spring element, then allowed to assume its operational configuration once inside the pleural space. As in other embodiments, holes 88 in catheter 80 permit the delivery of glue or other adhesive under pressure, such as from a syringe; the shape of the catheter and distribution of the holes help ensure even distribution of the adhesive material. In addition, the catheter may be moved within the pleural space after introduction of the adhesive material to rake or spread the material within the pleural space. Catheter 80 is returned to its delivery configuration for removal from the patient, such as by inward camming action caused by pulling catheter 80 back into the distal end of a chest tube.

Figure 9:
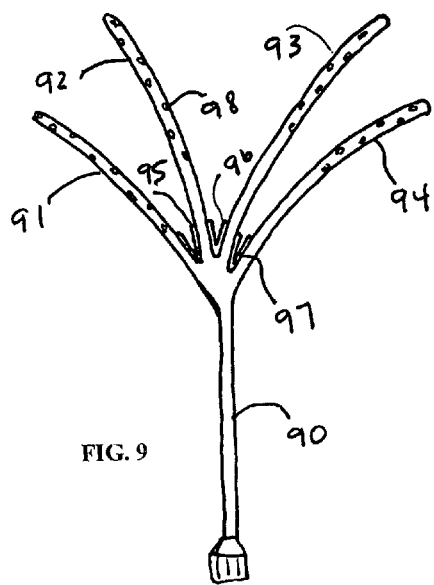
FIG. 9 shows a delivery catheter similar to that of FIG. 8, but with four branches.

FIG. 9 shows a delivery catheter 90 similar to that of FIG. 8 but with four branches 91-94 and three spring elements 95-97 separating the branches into the operational configuration shown. Holes 98 in catheter 90 permit the delivery of glue or other adhesive under pressure, such as from a syringe; the shape of the catheter and distribution of the holes help ensure even distribution of the adhesive material. In addition, the catheter may be moved within the pleural space after introduction of the adhesive material to rake or spread the material within the pleural space. Catheter 90 is returned to its delivery configuration for removal from the patient, such as by inward camming action caused by pulling catheter 90 back into the distal end of a chest tube.

Figure 10:
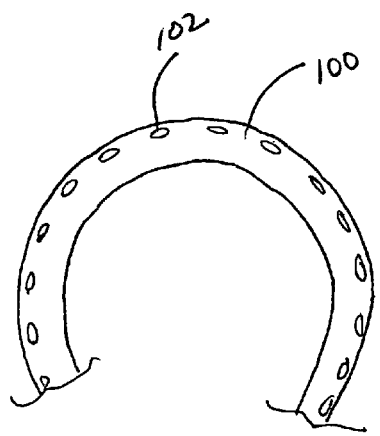
FIG. 10 shows an arrangement of holes on an adhesive delivery catheter.
Figure 11:
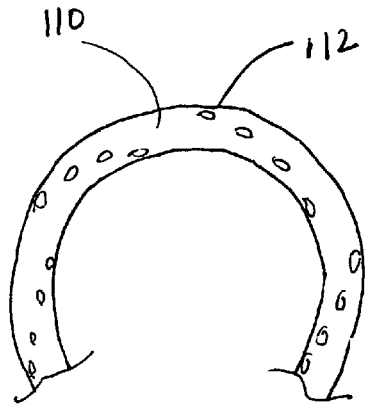
FIG. 11 shows an alternate arrangement of holes on an adhesive delivery catheter.

The arrangement of the holes in the delivery catheter may be modified to help provide even distribution of adhesive material within the pleural space. For example, FIG. 10 shows holes 102 in catheter 100 arranged along the outward facing side of a bend in catheter 100, and FIG. 11 shows holes 112 spiraling around catheter 110.

Figure 12:
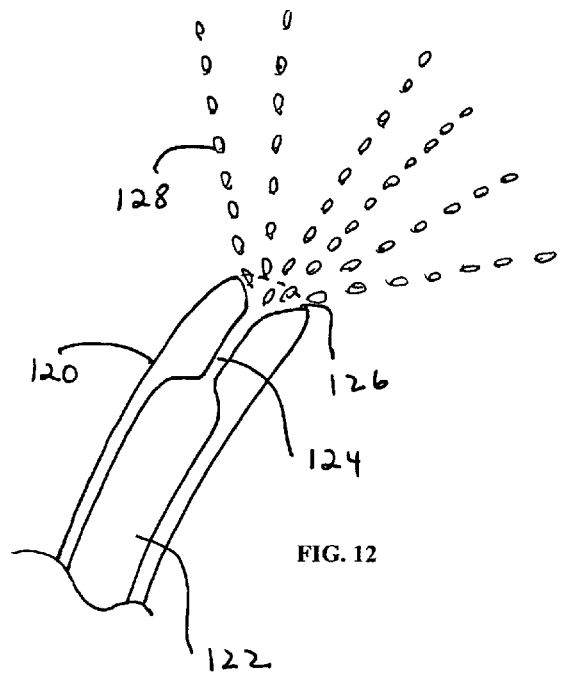
FIG. 12 shows a delivery channel having a narrowed delivery port.

As an alternative to a delivery catheter with multiple adhesive material delivery holes, the delivery catheter may have a single delivery port. For example, the delivery catheter 120 shown in FIG. 12 has a delivery channel 122 leading through a narrowed portion 124 to a single delivery nozzle 126 configured to spray adhesive material 128 around the pleural space.

Figure 13:
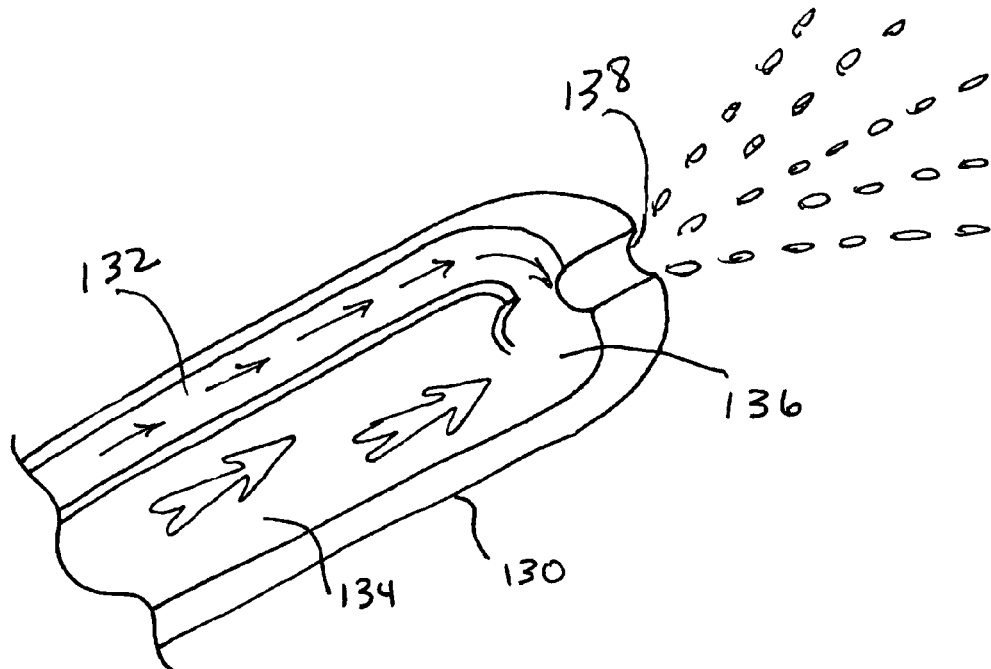
FIG. 13 shows a dual channel delivery channel.

Some adhesives may be formed as two-part compositions. FIG. 13 shows a delivery catheter 130 with two channels, 132 and 134. The two parts of a two-part adhesive composition may be delivered down the separate channels of catheter 130, then allowed to mix in a mixing chamber 136 before being sprayed out of a nozzle or delivery port 138.

Figure 14:
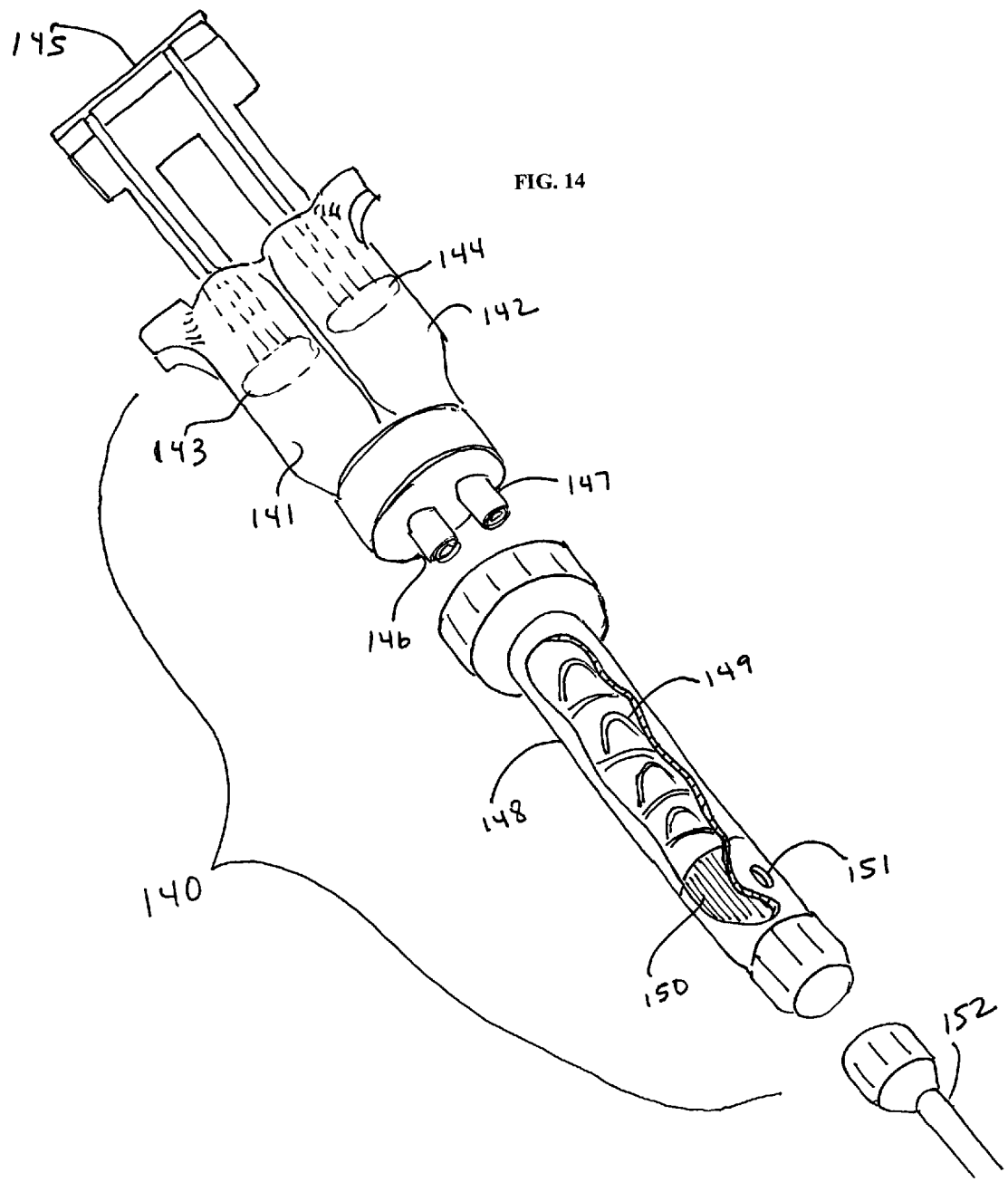
FIG. 14 shows an adhesive delivery system according to an embodiment of the invention.

FIG. 14 shows an alternative adhesive delivery system 140 in which the two parts of a two-part adhesive are delivered from separate syringe chambers 141 and 142 by moving plungers 143 and 144 tied together with a common actuator 145. The adhesive components are injected from sealed tips 146 and 147 into a detachable mixing chamber 148. Mixing chamber 148 may have prongs (not shown) that interact with tips 146 and 147 to break their seals when mixing chamber 148 is connected to the syringe. Baffles 149 or other mixing devices within mixing chamber 148 help ensure thorough mixing of the adhesive components. The mixing chamber 148 connects to a delivery catheter 152 which may be inserted into a patient's pleural space. The mixing chamber may have a porous plug or other filter 150 and an air bleed hole 151 at its distal end. Suitable plugs are microfiters available from Gen-Probe. The filter properties are such that air can be dispersed through the filter transverse to the axis of the glue while the glue will be forced axially through the filter.

Figure 15:
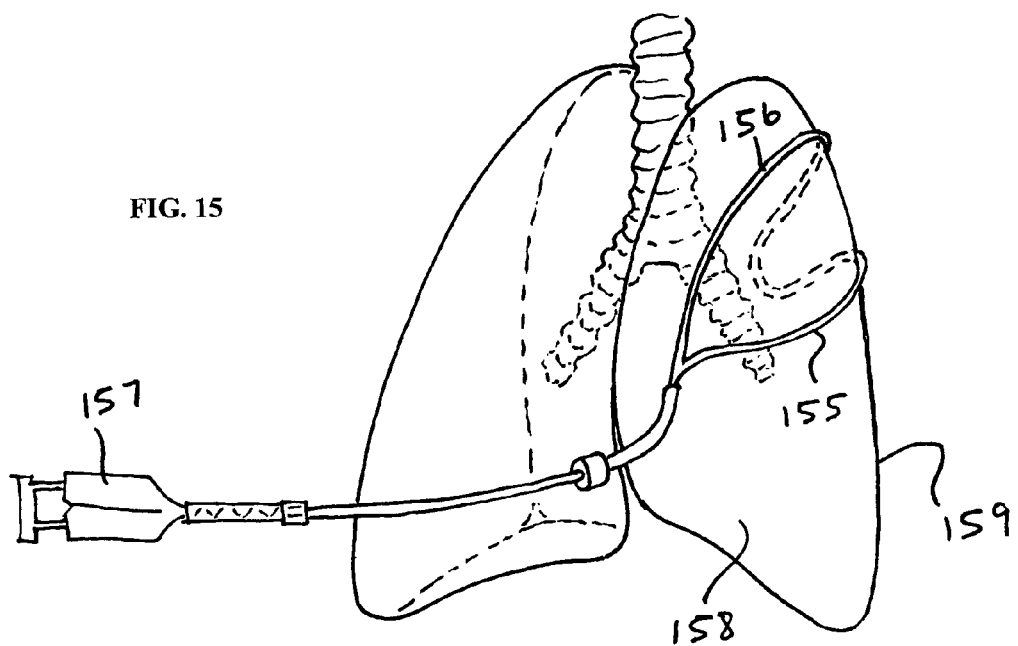
FIG. 15 shows an adhesive delivery catheter delivering adhesive to lung pleurae.

FIG. 15 shows an adhesive delivery catheter 154 that has branches 155 and 156 that spread and wrap around anterior 158 and posterior 159 sides of the lung within the pleural space. Adhesive material may be delivered from syringe 157 to the pleural space via holes (not shown) in the branches 155 and 156 of catheter 154.

Figure 16:
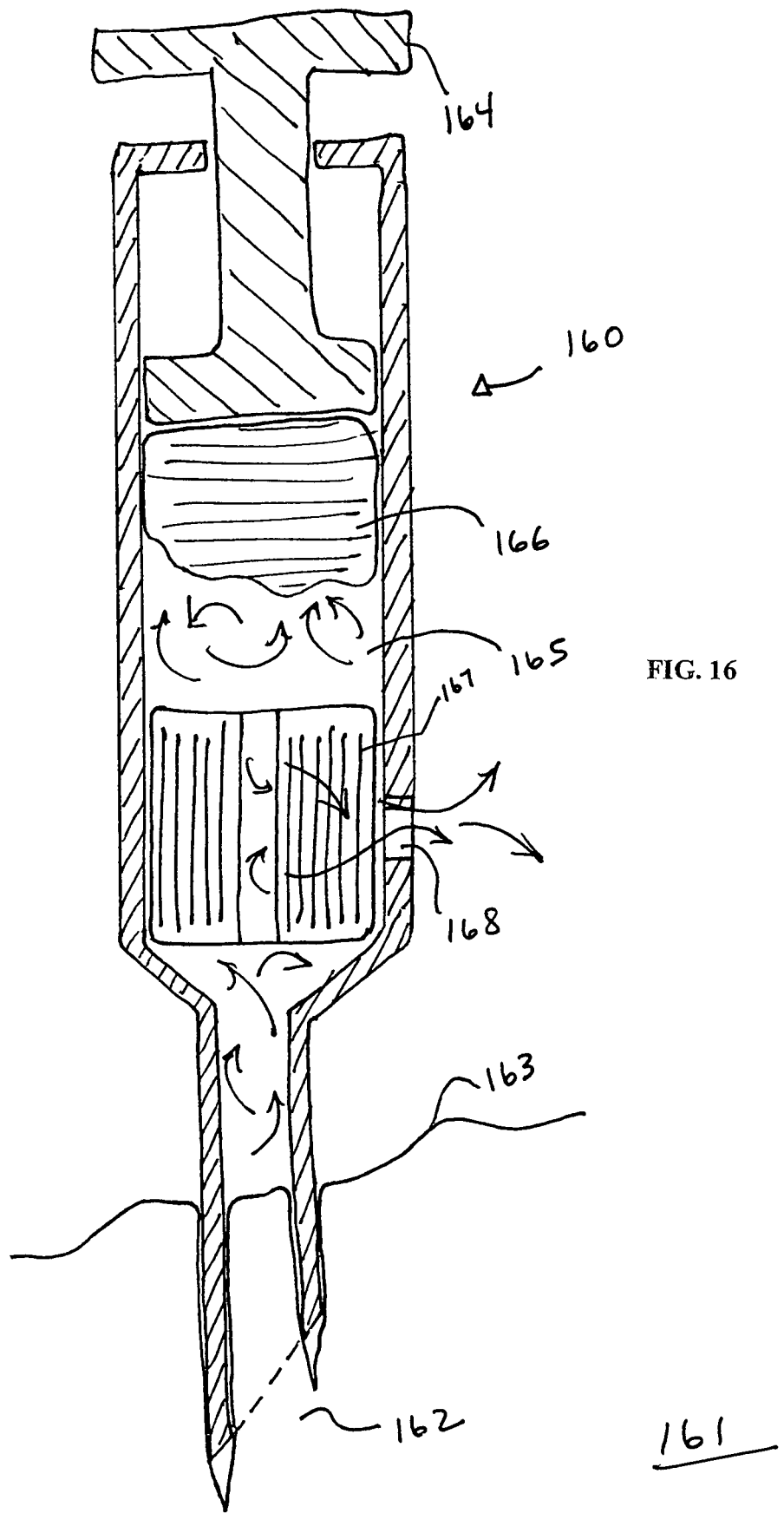
FIG. 16 shows an adhesive delivery device that provides percutaneous access to a pleural space.

FIG. 16 shows an adhesive delivery device 160 that provides percutaneous access to a pleural space 161 without the use of a chest tube. Device 160 has a sharp beveled distal end 162 that can pierce the patient's skin 163. A plunger 164 may be moved within a syringe portion 165 of device 160 to move adhesive material 166 through a porous plug 167 or other filter and into the patient. An air bleed hole 168 may be provided to permit trapped air to escape.

As will be appreciated by those of skill in the art, the delivery device can be used by using a single tube to drain fluid within the pleural space and then deliver the adhesive material which acts as a sealant to prevent the passage of liquid or gas. Alternatively, the fluid can be left within the pleural space, the delivery device can be inserted between the pleural layers and then maneuvered into place before delivering the sealant. In this scenario, it may be desirable to drain the fluid from the pleural space before delivering the sealant. Suitable sealants will cure within, approximately, 20 seconds to 1 minute, to enable the curing process to proceed without being effected by movement of the lungs during breathing.

Although many alternative sealant formulations may be suitable for this purpose, a preferred sealant would consist of primarily a combination of stable polyaldehyde, albumin and collagen with or without additional additives. The sealant can also have agents that initiate or accelerate the clotting cascade so the sealant can be used as a hemostatic agent. For example, a suitable material is described in US Patent Application Publ. No. 2004/0081676. This sealant works as a biologic glue that cures within a few minutes to seal pleural layers without causing inflammation or heat. The glue's intrinsic viscosity can be tuned to allow for fast or slow delivery through a delivery system, such as those shown above and includes glue viscosity more than 1.1 centipoise. This glue formulation is appropriate for use with all lung tissue and structures within the pulmonary system as well as pulmonary vasculature. It can also be formulated and used for any adhesive or anti-adhesion purpose including anastomosis of blood vessels and bronchi/bronchioles and to seal pulmonary structures from air leaks, bleeding or fluid leaks. Ideally, the sealant will cure within a few minutes, works well in a damp or wet environment, and blocks air or fluid from entering the pleural cavity. Typically, the glues are composed of a condensation product of glutaraldehyde that consists of cross-linked albumin, including porcine albumin. Adhesion values for the glue can be up to 1.5 psi, more preferably between 0.2-0.6 psi.

As described above, two-part sealants may be used with this invention. Sealant components for this application may include fibrin/thrombin, activated PEG/PEG-diamine, albumin/PEG, and albumin/glutaraldehyde sealants. The sealant is an implantable material that may contain hemostatic agents such as chitin derivatives including but not limited to carboxymethyl chitin and chitosan (1-100% deacetylated). The sealant components may also contain additives that affect viscosity, set time, adhesion, and biocompatibility. The albumin component may be formulated in weight to weight ratios of 10-50% where the remaining mass balance is aqueous solutions of salts, buffers, and additives or combinations thereof. The other component of the sealant is a cross-linker containing glutaraldehyde or derivatives thereof in weight to volume ratios of 1-25% where the remaining balance is an aqueous solution with or without additives, salts, or buffers or combinations thereof. These solutions may be applied from dispensers that deliver a ratio of 1 unit volume of protein solution per 1 unit volume of cross-linker solution (1:1 protein:cross-linker) and may be applied in ratios up to 10 unit volumes of protein solution per unit volume of cross-linker solution. Furthermore, mixing may occur by passing the solutions through a static mixing tip with helical or other geometrical devices that enhance the mixing efficiency. Sealants prepared from these solutions contain 5-45% protein and 0.5-14% crosslinker.

Other suitable sealants and other agents are described in US Pat. Appl. Publ. No. 2004/0052850; US Pat. Appl. Publ. No. 2004/0081676; U.S. Ser. No. 11/008,577; U.S. Ser. No. 11/008,092; U.S. Ser. No. 11/008,094; U.S. Ser. No. 11/008,578; U.S. Ser. No. 11/008,649; U.S. Ser. No. 11/008,777; U.S. Ser. No. 11/008,087; U.S. Ser. No. 11/008,093; U.S. Ser. No. 11/008,580; and U.S. Ser. No. 11/008,782.

Materials that solidify such as glue compositions form a structure that is typically stiffer than the intrinsic stiffness of lung tissue. Specifically, pull tests of lung parenchyma (comprised of alveolar sacks and collagen) sections show that the composite stiffness is very low. When agents are combined that form a stiffer structure than the underlying biomaterial or lung tissue, the modulus mismatch causes irritation, inflammation, tissue thickening, fibrosis, a remodeling cascade and adhesions that will promote and maintain lung volume reduction. Compositions that dry out or maintain viscosity levels above 2 centipoise (a measure of dynamic viscosity) generate shear and cause this stiffness mismatch to promote adhesions. Agents and hydrogel materials thicker than 10 centipoise work better. The glutaraldehyde glue technology employed can produce compositions that have 15 centipoise viscosity and higher levels up to and beyond 150 centipoise. By increasing the glue cross-linking properties, agents can be delivered that solidify to a gel or harder substance. Materials that gel to produce solids with a modulus greater than 10-20 centimeters of $H_2O$ will produce this same effect. Materials that are stiffer in a range between 20 and 100 centimeter of $H_2O$ are better. Materials that are stiffer than 100 cm $H_2O$ are preferable. Implantable materials with viscosity enhancing agents to promote these effects can be manufactured.

Many of these agents cause tissue binding to form localized adhesions or a bio-response that will help maintain permanent pleurae bonding. Introduction of these materials instigates one or more elements of a tissue remodeling cascade process. The process includes tissue polymer decomposition and/or necrosis that leads to recruitment of cellular respondents that include one or more of the following: Neutrophils, white blood cells, macrophages, CD8+, MMP's, Interlukens, cytokins and protocylins. The tissue then remodels to initiate tissue formation and thickening that culminates in the formation of tissue adhesions.

Other materials that can initiate this effect are cadmium, smoke artifacts, tars, materials that irritate tissue such as alcohols, solvents, organic solvents, acids, materials that are basic and materials that are acidic. These materials include compounds or compositions that have pH levels between 1 and 6.9 with materials closest to 1 being a preferable acid material. Additionally, compounds or materials that have pH levels between 7.5 and 14 work very well; materials closest to 14 work best.

When applying an adhesive material of the present invention, such as an implantable hydrogel comprised of a biocompatible material, or an implantable liquid that undergoes a physical transition from a liquid to a gel or other solid such as solid adhesives, control of deposition is very important. Ways of controlling deposition include localized dispensing of the sealant through a suitable device containing a lumen, and also through the addition of agents that increase the viscosity of one or more components of the implantable material. Such agents include biocompatible materials with viscosities that are greater than those of water, and include glycerol, polymeric materials such as proteins, carbohydrate-based polymers and derivatives thereof, synthetic materials including polyethylene glycols (PEG), polyethylene oxides (PEO), polyvinyl pyrrolidone (PVP), polyvinyl alcohol and other components described in the "United States Pharmacopeia" and the "Handbook of Pharmaceutical Excipients", edited by A. H. Kibbe. Other materials for controlling viscosity include oils, lipids, and fatty acids, including oleic acid, and phosphocholines. Phase separation can be controlled with emulsifiers including poly sorbate. For sealants prepared by mixing two or more components, the viscosities of one or more of the components can be modified by adding an appropriate agent to control spreading after application. Viscosities of these components can range from 1 to 1000 centistokes (a measure of kinematic viscosity).

Deposition and control of spreading of sealants containing two or more components are also affected by the gel time, or set time, of the mixed sealant. Sealants with short set times are preferable to those with longer set times. Set time can be controlled by the addition of set time modifiers, including agents that reduce or increase the set time relative to the corresponding formulation lacking the set time modifier. An example of an agent that decreases the set time is carboxymethyl cellulose. An example of an agent that increases the set time is glycerol.

Glutaraldehyde, as currently processed and used in some commercial sealants, undergoes reversible reactions that cause reoccurring inflammation. These properties can be improved by chemical modification of the glutaraldehyde. One such modification includes glutaraldehyde condensation reactions, as described in "Bioconjugate Techniques" by G. T. Hermanson. This condensation involves the formation of derivatives of glutaraldehyde in aqueous solutions containing acid or base. This reaction can be monitored by ultraviolet spectroscopy at or near 280 and 234 nanometers. At 280 nanometers, pure glutaraldehyde has significant absorbance, and little or no absorbance at 234 nanometers when measured as an aqueous solution at 0.5% weight to volume. When glutaraldehyde is chemically modified, it has significant absorbance at 234 nanometers. These derivatives are effective cross-linking agents when used with nucleophilic substrates such as proteins, including albumins. Furthermore, sealants prepared from glutaraldehyde derivatives are adhesive in vivo, through chemical or mechanical means, or a combination of chemical and mechanical means.

Implantable materials are adhesives, glues and sealants. For the present invention implantable materials include agents administered into tissue, including sealants, which may be comprised of hydrogels, proteins, or other biocompatible materials, that can be implanted into compromised tissue to benefit the patient. Examples of hydrogels include those prepared from natural sources including carbohydrate-based materials. Such materials include hyaluronans, hyaluronic acid, alginates, chitins, chitosans, and derivatives thereof. Proteins that enable the present invention include albumins, including porcine albumins, collagens, gelatins, and other proteins that can be cross-linked or that form solutions with viscosities greater than water. Other implantable materials include those prepared by mixing two or more components so that a viscous solution, gel, or solid is formed. Such implantable materials are prepared from a protein substrate where the protein is derived from natural, synthetic, or semi-synthetic processes. The protein may also be derived from recombinant DNA technology and may be isolated from cell-culture processes, as well as from transgenic plants and animals. Examples of proteins include albumins, collagens, and gelatins. Cross-linkers employed as part of the implantable material precursors include aldehydes, polyaldehydes, esters, and other chemical functionality suitable for cross-linking protein(s). Examples of homobifunctional cross-linking agents are described in "Bioconjugate Techniques" by G. T. Hermanson.

Materials of the invention, e.g., the cross-linked protein adhesives and heat-treated glutaraldehyde glues, when subjected to a swell test, have values in a percentile range lower than 100. To determine the swell test value, the material is placed in water and allowed to hydrate. The hydrated material is then weighed. Following the step of weighing the hydrated material, the hydrated material is then dried (e.g. by heating) and weighed again to determine a dry weight. The ratio of these two weights (hydrated vs. dry) comprises the result of the swell test and indicates how much moisture a material can take on in a percentage of its weight. Thus, for example, most non-glutaraldehyde glues typically have a swell test of 100-150%, which makes the glue come apart in a moist environment. Fibrin based glues have an even higher swell test value. Cross-linked albumin based glues of this invention have a lower swell test value which enables the glues to perform well in moist environments, with a swell test value ranging from −50% to 100%.

The implant components, including the cross-linking agent and the substrate, can be formulated at a pH in the range of 5-10 by adjusting the pH and/or by adding suitable buffers in the range of 1-500 mM. Examples of buffers include phosphate, carbonate, bicarbonate, borate, or imidazole, or mixtures thereof. Additionally, additives or stabilizers may be added to improve the stability of one or more of the components. Furthermore, imaging agents may be added to allow for detection of the material. Such agents include iodine, iodine compounds, metals such as gadolinium, radioisotopes, and other compounds for gamma scintigraphy, magnetic resonance imaging, fluoroscopy, CT, SPECT and other imaging modalities. Additionally, the material may be formulated such that the mechanical properties are suitable for applications in the specific tissue to which the implantable material is applied. Such properties include elasticity, modulus, stiffness, brittleness, strain, cohesion, adhesion, and stress. Agents for modifying the properties include fillers, plasticizers, and adhesion modifiers. Furthermore, the implant may induce a natural adhesive mechanism with or without the addition of chemical agents which may be added to the implant to induce a natural response. Such agents include particles in the range of 100 nm to 1 millimeter. Agents include chemical or biochemical agents (proteins or nucleic acids) that induce a natural response. Examples of such agents include bleomycin, cytokines and chemokines, and single stranded RNA molecules.

In some embodiments, it may be desirable to use bioabsorbable sealants that expand or swell in the presence of aqueous fluids such as biological fluids. A commonly used sealant of this type includes both natural and synthetic hydrogels. Synthetic hydrogels can be prepared from the following classes of polymers and these are generally considered to be non-biodegradable: poly (hydroxyalkyl methylacrylates) such as poly(glyceryl methacrylate)poly(acrylamide) and poly(methacrylamide) and derivativespoly(N-vinyl-2-pyrrolidone)anionic and cationic hydrogelspoly(vinyl alcohol) poly(ethylene glycol) diacrylate and derivatives from block copolymers composed of poly(ethylene oxide)-poly(propylene oxide)-poly(ethylene oxide) and poly(propylene oxide)-poly(ethylene oxide)-poly(propylene oxide) blocks, respectively. All of these materials can be cross-linked with agents such as ethylene glycol dimethacrylate or methylene-bis-acrylamide. Biodegradable synthetic hydrogels can be prepared from polymers such as those listed above by incorporating one or more of the following monomers: Glycolide, Lactide, e-Caprolactone, p-Dioxanone and Trimethylene CarbonateIn addition. Exemplary hydrogels based on natural products include polypeptides such as gelatin and polysaccharide such as starch and dextran. These natural products can be further processed by cross-linking with formaldehyde, glutaraldehyde and various other dialdehydes.

The biologically compatible sealant of the present invention may also comprise a detectable label. The detectable labels suitable for use in the present invention include any composition detectable by spectroscopic, photochemical, biochemical, immunochemical, electrical, optical or chemical means. A wide variety of appropriate detectable labels are known in the art, which include luminescent labels, radioactive isotope labels, and enzymatic labels. In preferred embodiments, one will likely desire to employ a fluorescent dye or label. These exemplary labels may be incorporated by a number of means well known to those of skill in the art. For instance, the label can be mixed with the sealant. Alternatively, labels can be chemically conjugated to the sealant molecules.

The use of a detectable label is particularly desirable for imaging the pleural region. The specific imaging means will depend on the particular type of label being used. For instance, radioactive labels can be detected by X-ray imaging. Fluorescent labels can be detected by an array of fluoroscopic equipment commonly employed by artisans in the field.

Ideally the composition of the sealant enables it to perform in a wet tissue environment. As is known in the art and discussed above, fibrin glue alone does not operate well in a wet environment and has been abandoned for use in many medical applications because of its inability to perform in a wet environment. The sealants used herein, in combination with the devices and methods, provide high adhesion in a wet environment. The adhesion of the sealant is beyond a low threshold that fibrin provides in wet tissue.

In determining an appropriate sealant to use with the devices and methods, two pieces of thin collagen based tissue (e.g. 1 inch wide by 2 inches long) are submerged into water ($H_2O$) or saline. The glue or sealant to be tested is then applied to the surface of one of the pieces and the two pieces are placed together in the water bath. The testing environment and materials are maintained at 67-69° F. The glue or sealant joint between the two layers of collagen is formed within 2 minutes of removing the tissue from the fluid without benefit of drying. The test section is 1 square inch of overlapped tissue that is glued with the excess tissue extending out both ends so that the two pieces can be gripped independently. The ends are gripped and pulled in opposite directions to test the force to shear the 1 inch section apart. The result is measured as shear stress or shear pressure and is recorded as pounds force per unit area. Currently available fibrin glues tested using this method fail at approximately 0.0-0.2 pounds force per square inch. Sealants and glues with a composition suitable for this invention fail at levels above 0.2 to well above 3.0 depending on the formulation.

In determining an appropriate sealant to use in another embodiment, the sealant is tested for biocompatibility based on MEM Elusion tests and the Agar Overlay tests.

In the MEM Elusion test, solids with uniform surface area and thickness of around <0.5 mm: 120 cm$^2$, solids with uniform surface area and thickness >0.5 mm: 60 cm$^2$, solids without uniform surface area of 4 grams, or liquids up to 10 mL are tested. The samples are extracted in a serum-supplemented mammalian cell culture media (MEM). Extractions may be performed in 0.9% saline or cell culture media without serum if desired. Samples are then extracted for 24-25 hours at 37±1° C. in 5±1% $CO_2$. The extracts are then filtered and placed in contact with a monolayer of L-929 cells (mouse fibroblasts). The cells are incubated at 37±2° C. in 5±1% $CO_2$ for 48±3 hours, 72±3 hours or whatever incubation time is desired. The cells are then scored for cytopathic effect. The L929 cell line is the most commonly used for the test, however, as will be appreciated by those skilled in the art, other cell lines may be suitable as well.

Agar Overlay tests typically are used for solids of 300 mm$^2$ or 300 mg and liquids of 3 mL. In the Agar Overlay test, a layer of agarose mixed with cell culture media is placed on top of a monolayer of L929 cells (mouse fibroblasts). The samples are placed on top of the agar layer. The cells are incubated for a minimum of 24 hours at 37±1° C. in 5±1% $CO_2$. The cells are scored for cytopathic effect. The L929 cell line is most commonly used for testing. However, as will be appreciated by those skilled in the art, other cell lines can be used without departing from the scope of the invention.

Using either the MEM Elusion test or the Agar Overlay test result, the sealant should have a cytotoxicity, on a scale from 0-4, of 0 or 1, even if the sealant has glutaraldehyde to improve adhesion in the composition.

The amount of pharmacologically active ingredient administered and the dosing regimen used will, of course, be dependent on the particular drug selected, the age and general condition, or the pharmacological condition of the subject being treated, the severity of the subject's condition, and the judgment of the prescribing physician.

The above descriptions with reference to certain illustrated embodiments and certain exemplary practices are provided as a guide to a practitioner of ordinary skill in the art, and are not meant to be limiting in any way.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of treating a patient for pleural effusion, the method comprising:
   percutaneously delivering an effective amount of an adhesive material to a pleural space of the patient by ejecting the adhesive material from a lumen of a percutaneous delivery device into the pleural space so as to cause a visceral pleura and a parietal pleura of the patient to adhere to one another such that excess fluid flow into the pleural space is inhibited; and
   mixing components of the adhesive material in the delivery device prior to the ejecting step,
   wherein the adhesive material has an adhesive strength up to 1.5 psi.

2. The method of claim 1 further comprising moving the delivery device from a delivery configuration to an operational configuration.

3. The method of claim 1 wherein the delivering step comprises delivering the adhesive material to the pleural space without delivering a fibrosis inducing material to the pleural space.

4. The method of claim 1 further comprising spreading the adhesive material within the pleural space.

5. The method of claim 1, wherein the adhesive material comprises a material selected from the group consisting of hydrogels, proteins, polymers and cross-linking agents.

6. The method of claim 5, wherein the hydrogel material comprises a material selected from the group consisting of hyalurons, hyaluronic acid, alginates, chitins, and chitosans.

7. The method of claim 5, wherein the protein material comprises a material selected from the group consisting of albumins, porcine albumin, collagens and gelatins.

8. The method of claim 5, wherein the polymer material comprises a material selected from the group consisting of poly(lactic acid) and poly(glycolide).

9. A method of treating a patient for pleural effusion, the method comprising:
   percutaneously inserting a pleural space access member into the patient, wherein the pleural space access member comprises a suction device and a device for delivering an adhesive material; and
   percutaneously delivering an effective amount of an adhesive material to a pleural space of the patient by ejecting the adhesive material from a lumen of a percutaneous delivery device into the pleural space so as to cause a visceral pleura and a parietal pleura of the patient to adhere to one another such that excess fluid flow into the pleural space is inhibited,
   wherein the adhesive material has a viscosity level of 1.1 centipoise or higher.

10. The method of claim 9 further comprising applying suction to the pleural space prior to delivering the adhesive material to the pleural space.

11. The method of claim 10 wherein the applying step comprises applying suction through the pleural space access member and the delivering step comprises delivering the adhesive material through the pleural space access member.

12. A method of treating a patient for pleural effusion, the method comprising:
   percutaneously delivering an effective amount of an adhesive material to a pleural space of the patient by ejecting the adhesive material from a lumen of a percutaneous delivery device into the pleural space so as to cause a visceral pleura and a parietal pleura of the patient to adhere to one another such that excess fluid flow into the pleural space is inhibited;

wherein the delivering step comprises delivering the adhesive material having an adhesive strength up to 1.5 psi.

13. A method of treating a patient for pleural effusion, the method comprising:

percutaneously delivering an effective amount of an adhesive material to a pleural space of the patient by ejecting the adhesive material from a lumen of a percutaneous delivery device into the pleural space so as to cause a visceral pleura and a parietal pleura of the patient to adhere to one another such that excess fluid flow into the pleural space is inhibited;

wherein the delivering step comprises delivering the adhesive material having an adhesive strength of between 0.2-0.6 psi.

14. A method of treating a patient for pleural effusion, the method comprising:

percutaneously delivering an effective amount of an adhesive material to a pleural space of the patient by ejecting the adhesive material from a lumen of a percutaneous delivery device into the pleural space so as to cause a visceral pleura and a parietal pleura of the patient to adhere to one another such that excess fluid flow into the pleural space is inhibited;

wherein the adhesive material having an adhesive strength up to 1.5 psi;

wherein the adhesive material comprises a material selected from the group consisting of hydrogels, proteins, polymers and cross-linking agents; and wherein the cross-linking agent material comprises a material selected from the group consisting of glutaraldehyde and stable polyaldehyde.

* * * * *